United States Patent [19]
Moser

[11] 4,231,921
[45] Nov. 4, 1980

[54] NOVEL LIGHT STABILIZERS
[75] Inventor: Paul Moser, Riehen, Switzerland
[73] Assignee: Ciba-Geigy Corporation, Ardsley, N.Y.
[21] Appl. No.: 922,875
[22] Filed: Jul. 10, 1978
[30] Foreign Application Priority Data Jul. 15, 1977 [CH] Switzerland .......................... 8793/77

[51] Int. Cl.$^2$ ...................... C08K 5/35; C07D 211/94; C07D 211/98; C07D 211/10
[52] U.S. Cl. ...................... 260/45.75 R; 260/45.75 W; 260/45.75 N; 544/69; 544/96; 546/68; 546/11
[58] Field of Search .................. 260/293.63, 45.8 NP, 260/293.9, 45.75; 546/6, 11; 544/64, 96

[56] References Cited
U.S. PATENT DOCUMENTS 3,705,166  12/1972  Murayama et al. ............... 260/293.9
4,046,737   9/1977  Holt et al. ..................... 260/45.8 NP

FOREIGN PATENT DOCUMENTS 2625967  7/1977  Fed. Rep. of Germany .
7614548  1/1977  Netherlands .

Primary Examiner—V. P. Hoke
Attorney, Agent, or Firm—Luther A. R. Hall

[57] ABSTRACT

Novel compounds of the general formula I

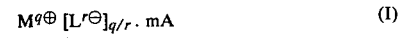

$$M^{q\oplus} [L^{r\ominus}]_{q/r} \cdot mA \qquad (I)$$

wherein $M^{q\oplus}$ is a metal ion carrying a double or triple positive charge and q is 2 or 3 and r is 1 or 2, the quotient q/r being 1, 1.5, 2 or 3, and L is a piperidine which is substituted by at least one enolate group in the 1-position or 4-position and wherein the ring nitrogen is sterically hindered by alkyl substituents in the adjacent positions, and m is 0, 1 or 2 and A is H2O or an amine.

10 Claims, No Drawings

NOVEL LIGHT STABILIZERS

The present invention relates to novel compounds containing enol groups, their metal chelates, their preparation and their use as light stabilisers in organic material, and also to the organic material protected with the aid of these compounds.

Metal complexes with sterically hindered amines and anions carrying a single charge have been described as stabilisers for synthetic polymers in German Offenlegungschrift No. 2,625,967.

It is the object of the present invention to provide novel compounds containing enol groups, and their chelate complexes with metal cations carrying a double or triple charge, which are distinguished by a good light-stabilising action and good stability to extraction and have good compatibility in polymers.

The novel compounds have the general formula I

in which $M^{q\oplus}$ is a metal ion carrying a double or triple positive charge and q is 2 or 3 and r is 1 or 2, the quotient q/r being 1, 1.5, 2 or 3, and L is a piperidine which is substituted by at least one enolate group in the 1-position or 4-position and in which the ring nitrogen is sterically hindered by alkyl substituents in the adjacent positions, and m is 0, 1 or 2 and A is $H_2O$ or an amine.

The present invention relates in particular to compounds of the formula I in which $M^{q\oplus}$ is a metal ion carrying a double or triple positive charge and q is 2 or 3 and r is 1 or 2, the quotient q/r being 1, 1.5, 2 or 3, and L is a group of the formula II

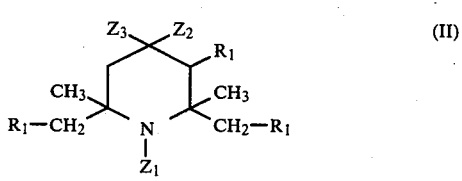

in which $R_1$ is hydrogen or $C_1$–$C_4$ alkyl and $Z_1$ is hydrogen, $C_1$–$C_{12}$ alkyl, $C_3$–$C_8$ alkenyl, $C_3$–$C_4$ alkynyl, $C_2$–$C_{21}$ alkoxyalkyl, $C_7$–$C_8$ aralkyl, an aliphatic acyl group having 1–4 C atoms, or one of the groups —$CH_2COOR_2$ or —$CH_2$—$CH(R_3)$—$OR_4$, or a —$(CH_2)_4$—$R_5$, —$CH_2$—$CH=CH$—$CH_2$—$R_5$,

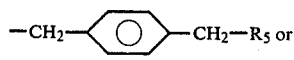 or

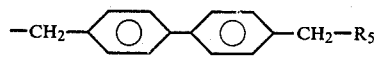

radical or a group of the formula III

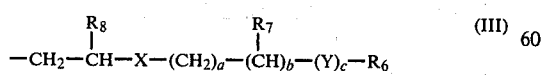

in which $R_2$ is $C_1$–$C_8$ alkyl, $C_3$–$C_6$ alkenyl, phenyl, $C_7$–$C_8$ aralkyl or cyclohexyl and $R_3$ is hydrogen, methyl or phenyl and $R_4$ is an aliphatic $C_1$–$C_{18}$ acyl group, an aromatic $C_7$ acyl group, an araliphatic $C_8$–$C_9$ acyl group or an alicyclic $C_6$–$C_9$ acyl group, in which the aromatic part can be unsubstituted or substituted by chlorine, $C_1$–$C_4$ alkyl, $C_1$–$C_8$ alkoxy, and/or hydroxyl, and $R_5$ is a group of the formula IV

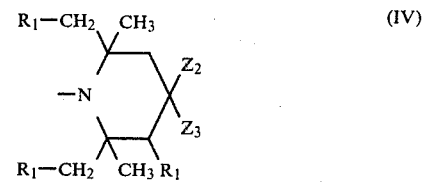

in which $R_1$, $Z_2$ and $Z_3$ are as defined below, and $R_6$ is a group of the formula V

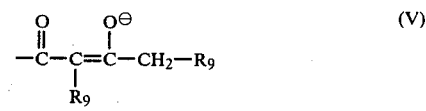

in which $R_9$ is hydrogen or $C_1$–$C_4$ alkyl, and $R_7$ and $R_8$ independently of one another are hydrogen, methyl, phenyl, $C_2$–$C_9$ alkoxymethyl or a —$CH_2$—$O$—$R_6$ radical, in which $R_6$ is as defined above, and a is 0, 1 or 2 and b is 0 or 1 and c is 0 or, if a and/or b differ from 0, is also 1, and X and Y independently of each other are -O- or

in which $R_{10}$ is hydrogen, $C_1$–$C_{12}$ alkyl, $C_3$–$C_8$ alkenyl, cyclohexyl, $C_3$–$C_{21}$ alkoxyalkyl, $C_7$–$C_{13}$ aralkyl, phenyl which is unsubstituted or substituted by $C_1$–$C_8$ alkyl and/or $C_1$–$C_8$ alkoxy, or a group —$CH_2$—$CH_2$—$O$—$R_6$, in which $R_6$ is as defined above, and $R_{10}$ is also a group of the formula VI

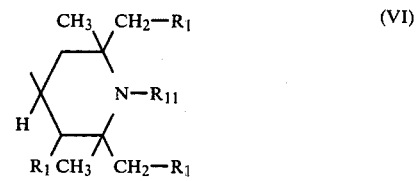

in which $R_1$ is as defined above and $R_{11}$ is hydrogen, $C_1$–$C_{12}$ alkyl, $C_3$–$C_8$ alkenyl, $C_2$–$C_{21}$ alkoxyalkyl, $C_7$–$C_8$ aralkyl, an aliphatic acyl group having 1–4 C atoms, or a group—$CH_2COOR_2$, in which $R_2$ is as defined above, and $Z_2$ is hydrogen, $C_2$–$C_{18}$ aliphatic acyloxy, benzoyloxy which is unsubstituted or substituted by $C_1$–$C_8$ alkyl or $C_1$–$C_8$ alkoxy, or a $C_2$–$C_{18}$ acylamido group which is unsubstituted or $C_1$–$C_8$ N-alkyl-substituted, or one of the groups —$R_{12}$, —$(CH_2)_d$—$R_{12}$,

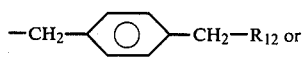 or

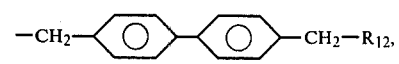

in which d is 2 to 10 and $R_{12}$ is a group of the formula VII

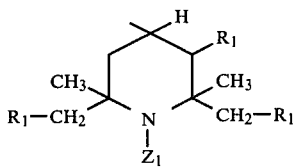
(VII)

in which $R_1$ and $Z_1$ are as defined above, or $Z_2$ is also a group of the formula VIII

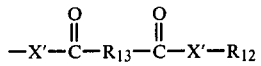
(VIII)

in which $R_{12}$ is as defined above and $X'$ is —O— or $$-\underset{|}{N}-R_{14},$$

in which $R_{14}$ is hydrogen or $C_1$–$C_4$ alkyl, and $R_{13}$ is —(CH$_2$)$_e$— or a group

in which e is 0 to 8 and $R_{15}$ and $R_{16}$ independently of each other are hydrogen, $C_1$–$C_{12}$ alkyl, $C_3$–$C_8$ alkenyl, $C_7$–$C_{11}$ aralkyl, cyanomethyl, cyanoethyl or a group —CH$_2$COOR$_{17}$, in which $R_{17}$ is methyl or ethyl, or $Z_2$ is one of the groups

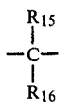
(IX)

(X)

$$-N-R_{21}-N-R_{12}$$ (XI)

in which $R_6$, $R_7$ and $R_{12}$ are as defined above and $R_{18}$ is hydrogen, $C_1$–$C_8$ alkyl, allyl, phenyl or benzyl and $R_{19}$ is hydrogen, $C_1$–$C_8$ alkyl, allyl or benzyl and $R_{20}$ is $C_1$–$C_4$ alkyl or a group of the formula V which is as defined above, and $R_{21}$ is $C_2$–$C_6$ alkylene, cyclohexylidene, phenylene, diphenylene, 4,4'-diphenylene oxide or 4,4'-diphenylenemethane, or $Z_2$ is also a group of the formulae XII, XIII or XIV $$-(X)_f-(CH_2)_a-(CH)_b-(Y)_c-(CH_2)_a-(CH)_b-(O)_g-R_6$$ (XII)

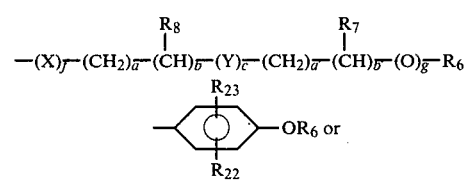
(XIII)

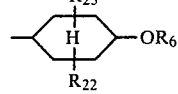
(XIV)

in which a, b, c, X, Y, $R_6$, $R_7$ and $R_8$ are as defined above and f, a' and b' are 0 or 1 and g is 0 or, if a' and/or b' differ from 0, is also 1, and $R_{22}$ and $R_{23}$ independently of one another are hydrogen, $C_1$–$C_4$ alkyl, cyclohexyl, phenyl, benzyl, α-methylbenzyl or α,α-dimethylbenzyl, and $Z_3$ is hydrogen or cyano, or $Z_2$ and $Z_3$ together are one of the groups XV, XVI or XVII $$\underset{O\diagdown_{\diagup}O}{CH_2\text{——}CH\text{—}CH_2\text{—}O\text{—}R_6}$$ (XV)

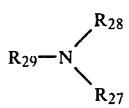
(XVI)

(XVII)

in which $R_6$ is as defined above and $R_{24}$ is hydrogen, methyl or ethyl and $R_{25}$ is hydrogen, $C_1$–$C_{18}$ alkyl, $C_3$–$C_8$ alkenyl, cyclohexyl, $C_7$–$C_8$ aralkyl or a group —CH$_2$—COOR$_{26}$ or —CH$_2$—CH(R$_8$)—O—R$_6$, in which $R_{26}$ is $C_1$–$C_{18}$ alkyl and $R_6$ and $R_8$ are as defined above, and m is 0, 1 or 2 and A is H$_2$O or an amine of the formula (XVIII)

$$R_{29}-N\diagup^{R_{28}}_{\diagdown R_{27}}$$ (XVIII)

in which $R_{27}$ is substituted or unsubstituted alkyl, cycloalkyl, aryl or aralkyl, a substituted or unsubstituted aminoalkyl group or a piperidinyl group, and $R_{28}$ is hydrogen or substituted or unsubstituted alkyl or cycloalkyl, a substituted or unsubstituted aminoalkyl group or a substituted or unsubstituted piperidinyl group, or $R_{27}$ and $R_{28}$ together with the N atom form a pyrrolidine, piperidine or morpholine ring which is substituted by alkyl groups or is unsubstituted, and $R_{29}$ is hydrogen or substituted or unsubstituted alkyl.

A cation M of the valency q is, for example a cation of the series $Mg^{2+}$, $Ca^{2+}$, $Sr^{2+}$, $Ba^{2+}$, $Zn^{2+}$, $Cd^{2+}$, $Al^{3+}$, $Sn^{2+}$, $Cr^{3+}$, $Co^{2+}$ and $Ni^{2+}$, an oxo complex of metal ions, especially $VO^{2+}$ and $MoO_2^{2+}$, or a tin-alkyl ion of the formula (R*)$_2$Sn$^{2+}$ or (CH$_2$CH$_2$COOR*)$_2$Sn$^{2+}$ in which R* is $C_1$–$C_8$ alkyl, but especially ethyl, n-propyl and in particular n-butyl; preferred cations M$^{q+}$ are especially $Ca^{2+}$, $Mg^{2+}$, $Zn^{2+}$ and $Co^{2+}$ and in particular $Ni^{2+}$ or $Al^{3+}$. The coordination numbers of these cations are known to those skilled in the art and are 4 or 6 depending on the metal.

q is 2 or 3, especially 2.

r is 1 or 2 and corresponds to the number of enolate anions in the ligand L. If the ligand L contains one enolate group, the complex as a rule contains q ligands L, unless a less than equivalent amount of L has been used for the preparation. If the ligand L contains two enolate groups, it is not necessary for the two enolic coordination positions to be occupied by one and the same metal centre $M^{q+}$. Ligands L containing two enolate groups are therefore suitable for the preparation of oligomeric or even polymeric molecules, which are distinguished by an increased stability to extraction. The ratio of the metal $M^{q+}$ to the ligand $L^{r-}$ indicated in the formula I is also correct in this case if it is calculated for the structural unit on which the polymer is based. Such compounds are novel and have a molecular weight of about 400–10,000, preferably of 400–2,000.

As $C_1$–$C_4$ alkyl, $R_1$ is branched or, especially, unbranched alkyl, such as ethyl, n-propyl or n-butyl, but in particular methyl. Preferably, $R_1$ is hydrogen. Preferably all the symbols $R_1$ have the same meaning.

As $C_1$–$C_{12}$ alkyl, $Z_1$ is, for example, methyl, ethyl, n-propyl, n-butyl, n-pentyl, n-octyl, n-decyl or n-dodecyl. Preferred alkyl groups are those having 1–8 C atoms and especially those having 1–4 C atoms, and in particular methyl.

As $C_3$–$C_8$ alkenyl, $Z_1$ is, for example, allyl, 2-butenyl, 2-hexenyl or 2-octenyl, especially allyl.

As $C_3$–$C_4$ alkynyl, $Z_1$ is, for example, propargyl.

If $Z_1$ is $C_2$–$C_{21}$ alkoxyalkyl, the alkyl moiety can contain 1–3 C atoms and the alkoxy moiety can consist of 1–18 C atoms, as, for example, in methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl. Compounds to be mentioned in particular are those in which $Z_1$ is an alkoxyalkyl group having 2–6 C atoms.

As $C_7$–$C_8$ aralkyl, $Z_1$ is, for example, benzyl or α-phenylethyl.

As an aliphatic acyl group having 1–4 C atoms, $Z_1$ is, for example, formyl, acetyl, acryloyl or crotonyl, especially acetyl.

If $Z_1$ is the group —CH$_2$COOR$_2$, $R_2$, as $C_1$–$C_8$ alkyl, is, for example, methyl, ethyl, isopropyl, n-butyl, isobutyl, t-butyl, isopentyl or n-octyl. Preferably, $R_2$ is $C_1$–$C_4$ alkyl. As $C_3$–$C_6$ alkenyl, $R_2$ is, for example, allyl, 2-butenyl or 2-hexenyl. As $C_7$–$C_8$ aralkyl, $R_2$ is, for example, benzyl or α-phenylethyl.

If $Z_1$ is the group —CH$_2$—CH(R$_3$)—OR$_4$, $R_3$ is hydrogen, methyl or phenyl, especially hydrogen. As an aliphatic $C_1$–$C_{18}$ acyl radical, $R_4$ is, for example, formyl, acetyl, propionyl, butyryl, octanoyl, dodecanoyl, stearoyl or acryloyl. As an aromatic $C_7$ acyl radical, $R_4$ is benzoyl, and as an araliphatic $C_8$–$C_9$ acyl radical, $R_4$ is cinnamoyl, phenylacetyl or phenylpropionyl. The aromatic part is unsubstituted or substituted by chlorine or $C_1$–$C_4$ alkyl, such as methyl, ethyl, n-propyl or t-butyl, or by $C_1$–$C_8$ alkoxy, such as methoxy, ethoxy, butoxy or octoxy, and/or hydroxyl. Substituted aromatic acyl groups are, for example, chlorobenzoyl, toluoyl, isopropylbenzoyl, 2,4-dichlorobenzoyl, 4-methoxybenzoyl, 3-butoxybenzoyl, 2-hydroxybenzoyl or 3,5-di-t.-butyl-4-hydroxybenzoyl. An araliphatic substituted acyl group is, for example, β-(3,5-di-t.-butyl-4-hydroxyphenyl)-propionyl. If $R_4$ is an alicyclic $C_6$–$C_9$ acyl group, this can be cyclohexylcarbonyl or 2,4-dimethylcyclohexylcarbonyl.

If $Z_1$ is one of the groups —(CH$_2$)$_4$—R$_5$, —CH$_2$—CH═CH—CH$_2$—R$_5$,

the symbols $R_1$, $Z_2$ and $Z_3$ in these formulae are as defined. In formula IV, $R_1$ is most preferably hydrogen. Preferred compounds of the formula I are those in which all of the radicals $R_1$ in the molecule are identical. The same applies for all of the radicals $Z_2$ and all of the radicals $Z_3$.

If $Z_1$ is a group of the formula III, $R_6$ in this formula is a group of the formula V, in which $R_9$ is $C_1$–$C_4$ alkyl, such as ethyl, propyl, n-butyl and especially methyl, and, most preferably, hydrogen.

As $C_2$–$C_9$ alkoxymethyl, $R_7$ and $R_8$ are, for example, methoxymethyl, ethoxymethyl, propoxymethyl, butoxymethyl or octoxymethyl. The preferred meaning of $R_7$ and $R_8$ is hydrogen or methyl. Particularly interesting compounds are those in which $R_7$ is hydrogen and $R_8$ is hydrogen or methyl.

X is —O— or

preferably —O—.

Y is —O— or

preferably

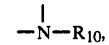

in which $R_{10}$ is most preferably hydrogen or also methyl.

As $C_1$–$C_{12}$ alkyl, $R_{10}$ is, for example, methyl, ethyl, n-propyl, n-butyl, n-pentyl, n-octyl, n-decyl or n-dodecyl, but preferably methyl.

As $C_3$–$C_8$ alkenyl, $R_{10}$ is, for example, allyl, 2-butenyl, 2-hexenyl or 2-octenyl, especially allyl.

If $R_{10}$ is $C_3$–$C_{21}$ alkoxyalkyl, the alkyl moiety can contain, especially, 2–3 C atoms and the alkoxy moiety can consist of 1–18 C atoms, for example 2-methoxyethyl, 2-ethoxyethyl, 2-n-butoxyethyl, 3-n-butoxyethyl, 2-octoxyethyl or 2-octadecyloxyethyl.

As $C_7$–$C_{13}$ aralkyl, $R_{10}$ is especially phenylethyl or in particular benzyl.

If $R_{10}$ is phenyl, it can be monosubstituted or disubstituted by $C_1$–$C_8$ alkyl, such as methyl, ethyl, propyl, butyl, hexyl or octyl, especially methyl. As phenyl, $R_{10}$ can also be disubstituted, and preferably monosubstituted, by $C_1$–$C_8$ alkoxy, such as methoxy, ethoxy, butoxy or octoxy, especially methoxy.

If $R_{10}$ is a group of the formula VI, $R_{11}$ in this formula, as $C_1$–$C_{12}$ alkyl, $C_3$–$C_8$ alkenyl, $C_2$–$C_{21}$ alkoxyalkyl or $C_7$–$C_8$ aralkyl, or as an aliphatic acyl group having 1–4 C atoms or as the group —CH$_2$COOR, can have the meaning indicated above by way of example for $Z_1$.

$Z_2$ can preferably be hydrogen.

If $Z_2$ is $C_2$-$C_{18}$, preferably $C_2$-$C_{12}$ and especially $C_2$-$C_7$ aliphatic acyloxy, it can be acetyloxy, propionyloxy, butyryloxy, hexanoyloxy, heptanoyloxy, dodecanoyloxy or stearoyloxy.

As benzoyloxy, $Z_2$ can be disubstituted, and preferably monosubstituted, by $C_1$-$C_8$ alkyl, such as methyl, ethyl, propyl, butyl or octyl, especially by methyl, or by $C_1$-$C_8$ alkoxy, such as methoxy, ethoxy, butoxy or octoxy, especially by methoxy; particularly interesting compounds are those in which $Z_2$, as benzoyloxy, is unsubstituted.

As $C_2$-$C_{18}$ acylamido, $Z_2$ is, for example, acetylamido, propionylamido, butyrylamido, hexanoylamido, heptanoylamido, dodecanoylamido or stearoylamido. Acylamido groups having 2-12 C atoms, and especially those having 2-7 C atoms, are preferred.

If $Z_2$ is a $C_1$-$C_8$ N-alkyl-substituted $C_2$-$C_{18}$ acylamido group, possible N-alkyl substituents are, for example, methyl, ethyl, n-propyl, n-butyl, n-hexyl or n-octyl.

If $Z_2$ contains a radical $R_{12}$, this radical can be linked to the piperidine ring directly or preferably via an alkylene group having 2-10 C atoms and preferably 2-6 C atoms, such as dimethylene, trimethylene, tetramethylene, hexamethylene or decamethylene. Linkages via a xylylene or bitolylene bridge are equally preferred as alkylene bridges.

$Z_2$ can be a group of the formula VIII in which $R_{13}$, as alkylene, can have, for example, 1-8 and preferably 1-6 C atoms, such as methylene, dimethylene, trimethylene, tetramethylene, hexamethylene or octamethylene. The index e can, however, just as preferably be 0, i.e. the alkylene group can also be omitted.

X' is —O— or $$-\overset{|}{N}-R_{14},$$

in which $R_{14}$, as $C_1$-$C_4$ alkyl, is ethyl, propyl or butyl, and the preferred meaning of $R_{14}$ is hydrogen or methyl.

$R_{13}$ can also be a group —$(R_{15})C(R_{16})$—, in which $R_{15}$ and $R_{16}$ can be $C_1$-$C_{12}$, and preferably $C_1$-$C_4$, alkyl, such as methyl, ethyl, propyl, butyl, hexyl, octyl or dodecyl.

As $C_3$-$C_8$ alkenyl, $R_{15}$ and $R_{16}$ are, for example, allyl, 2-butenyl, 2-hexenyl or 2-octenyl, especially allyl.

As $C_7$-$C_{11}$ aralkyl, $R_{15}$ and $R_{16}$ are especially phenylethyl or in particular benzyl.

$R_{15}$ and $R_{16}$ can be cyanoethyl and especially also cyanomethyl.

In the groups of the formulae IX or X, $R_{18}$, as $C_1$-$C_8$ alkyl, can be, for example, methyl, ethyl, propyl, butyl, hexyl or octyl. Preferably, however, $R_{18}$ is hydrogen.

In formula X, $R_{19}$, as $C_1$-$C_8$ alkyl and preferably $C_1$-$C_4$ alkyl, can be, for example, methyl, ethyl, n-propyl, n-butyl, hexyl or octyl. $R_{19}$ is also preferably hydrogen, allyl or benzyl.

In formula XI, $R_{20}$, as $C_1$-$C_4$ alkyl is, for example, methyl, ethyl, n-propyl or n-butyl. A preferred meaning of $R_{20}$ to be mentioned is, however, a group of the formula V.

In the formula XI, $R_{21}$ is most preferably $C_2$-$C_6$ alkylene, such as dimethylene, trimethylene, tetramethylene or hexamethylene. However, it can also preferably be cyclohexylidene or phenylene.

If $Z_2$ is a group of the formula XII, the indices a', b' and g in this formula are preferably 0.

In the formulae XIII and XIV, $R_{22}$ and $R_{23}$, as $C_1$-$C_4$ alkyl, can be, for example, methyl, ethyl, propyl or butyl; ethyl and especially methyl are preferred, as is also hydrogen.

If $Z_2$ and $Z_3$ together form a heterocyclic structure, groups of the formula XV and XVI are particularly preferred.

$R_{24}$ is then ethyl, preferably methyl and especially hydrogen.

As $C_1$-$C_{12}$ alkyl, $R_{25}$ is, for example, methyl, ethyl, propyl, butyl, hexyl, octyl, decyl or dodecyl. Alkyl groups having 1-8 C atoms are preferred.

As aralkyl having 7-8 C atoms, $R_{25}$ is in particular phenylethyl or especially benzyl.

As $C_3$-$C_8$ alkenyl, $R_{25}$ is, for example, allyl, 2-butenyl, 2-hexenyl or 2-octenyl, especially allyl.

As $C_1$-$C_{18}$ alkyl, $R_{26}$ is, for example, methyl, ethyl, propyl, butyl, hexyl, octyl, dodecyl or octadecyl. Preferred alkyl radicals are those having 1-12 and especially 1-8 C atoms and in particular those having 1-4 C atoms.

If A is an amine of the formula XVIII, the substituents $R_{27}$, $R_{28}$ and $R_{29}$ thereof are, for example, $C_1$-$C_{18}$ alkyl, such as methyl, ethyl, isopropyl, sec.-butyl, n-hexyl, n-octyl, n-decyl, n-dodecyl or n-octadecyl, most preferably $C_1$-$C_8$ alkyl.

If the said alkyl is substituted alkyl, it is in particular $C_1$-$C_{18}$ hydroxyalkyl, such as 1-hydroxyethyl, 1-hydroxypropyl, 1-hydroxy-1-methylethyl, 3-hydroxypentyl or 1-hydroxy-2-methyl-ethyl, preferably $C_1$-$C_8$ hydroxyalkyl.

$R_{27}$ and $R_{28}$ can also be $C_5$-$C_{12}$, and especially $C_5$-$C_6$ cycloalkyl, for example, cyclopentyl, cyclohexyl, 4-methylcyclohexyl or 4-tert.-butyl-cyclohexyl. $R_{27}$ can also be substituted or unsubstituted $C_6$-$C_{10}$ aryl, for example phenyl, tolyl, xylyl, tert.-butyl-phenyl or dodecylphenyl. As $C_7$-$C_{20}$ aralkyl, $R_{27}$ is, for example, benzyl, 4-methylbenzyl, 4-t.-butylbenzyl or 4-dodecylbenzyl, especially benzyl.

A substituted or unsubstituted aminoalkyl group represented by $R_{27}$ and $R_{28}$ is in particular an aminoalkyl group substituted by a piperidinyl group, for example an aminoalkyl group of the formula VIIb $$-(CH_2)_v-\overset{R_{14}}{\underset{|}{N}}\diagdown \overset{CH_3 \ \ CH_2-R_1}{\underset{R_1 \ CH_3 \ \ CH_2-R_1}{\diagup}} N-R_{11} \quad \text{(VIIb)}$$

in which $R_1$, $R_{11}$ and $R_{14}$ are as defined above and v is an integer from 1 to 8.

A substituted or unsubstituted piperidinyl group represented by $R_{27}$ and $R_{28}$ is preferably a piperidinyl grup of the formula VI.

$R_{27}$ and $R_{28}$ together with the N atom of the amine of the formula XVIII can form a pyrrolidine, piperidine or morpholine ring which is substituted by alkyl groups or is unsubstituted. In this case, the ring can be, for example, a 2,5-dimethylpyrrolidine, 4-methylpiperidine, 2,2,6,6-tetramethylpiperidine, 2,6-dimethylmorpholine, pyrrolidine, piperidine or morpholine ring, especially a 2,2,6,6-tetramethylpiperidine ring.

m can be 0, 1 or 2, preferably 0.

Thus, when the ligand A is an amine it is, as defined herein, a primary, secondary or tertiary amine which is able to form a complex with the metal chelates listed above. Examples of such amines are: n-butylamine, n-dodecylamine, β-ethylhexylamine, benzylamine, 4-octylbenzylamine, dibutylamine, dicyclohexylamine, dioctadecylamine, morpholine, 2,2,6,6-tetramethylpiperidine, N-ethylaniline, tri-n-octylamine, N,N-dimethylaniline, N,N-dimethyl-cyclohexylamine, N-ethylpiperidine, N-methylpyrrolidine, dibenzylpropylamine, N-benzyl-2,5-dimethylpyrrolidine, 4-dimethylamino-2,2,6,6-tetramethylpiperidine, 4-dimethylamino-1,2,2,6,6-pentamethylpiperidine, N,N'-methyl-N,N'-(1,2,2,6,6-pentamethyl-4-piperidyl)-ethylenediamine, hydroxyethylamine, di-(hydroxyethyl)-amine, tri-(hydroxyethyl)-amine, tri-(2-hydroxypropyl)-amine, N-phenyl-N,N-di-(hydroxyethyl)-amine or hydroxypropylamine.

The complexes according to the invention, of the formula I, contain, per mol of metal $M^{q\oplus}$, 0 to 2 mols of the amine ligand A, all or part of which can be replaced by water. The molar proportion expressed by m in the formula I is thus made up of the sum of m' mols of the amine ligand and m'' mols of water; the molar proportions expressed by m' and m'' do not need to be an integer. Preferred complexes are those which have a low water content since these dissolve in non-polar polymers better than do highly hydrated complexes. m' thus assumes approximately the value of m.

An amine ligand A is necessary only when the coordination number of the metal centre is not satisfied by the chelate-forming agent L alone.

Preferred compounds of the formula I are those in which $M^{q\oplus}$ is $Mg^{2+}$, $Ca^{2+}$, $Sr^{2+}$, $Ba^{2+}$, $Zn^{2+}$, $Cd^{2+}$, $Al^{3+}$, $Sn^{2+}$, $Cr^{3+}$, $Co^{2+}$, $Ni^{2+}$, $VO^{2+}$, $MoO^{2+}$, $(R^*)_2Sn^{2+}$ or $(CH_2CH_2COOR^*)_2Sn^{2+}$, in which $R^*$ is $C_1$-$C_8$ alkyl and q is 2 or 3 and r is 1 or 2, the quotient q/r being 1, 1.5, 2 or 3, and L is a group of the formula II, in which $R_1$ is hydrogen or methyl and $Z_1$ is hydrogen, $C_1$-$C_8$ alkyl, $C_3$-$C_4$ alkenyl, $C_3$ alkynyl, $C_2$-$C_{10}$ alkoxyalkyl, $C_7$-$C_8$ aralkyl, acetyl or one of the groups —$CH_2COOR_2$ or —$CH_2$—$CH(R_3)$—$OR_4$, or a —$(CH_2)_4$—$R_5$, —$CH_2$—$CH$=$CH$—$CH_2$—$R_5$,

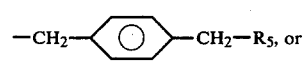

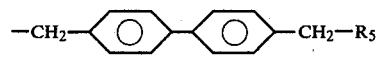

radical or a group of the formula III, in which $R_2$ is $C_1$-$C_4$ alkyl, $C_3$-$C_4$ alkenyl, phenyl, $C_7$-$C_8$ aralkyl or cyclohexyl and $R_3$ is hydrogen or methyl, $R_4$ is an aliphatic acyl group having 1-12 atoms and $R_5$ is a group of the formula IV, in which $Z_2$ and $Z_3$ are as defined below and $R_1$ is hydrogen, and $R_6$ is a group of the formula V, in which $R_9$ is hydrogen or methyl, and $R_7$ and $R_8$ independently of one another are hydrogen or methyl and a is 0, 1 or 2 and b is 0 or 1 and c is 0 or, if a and/or b differ from 0, is also 1, and X is —O— and Y is —O— or

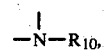

in which $R_{10}$ is hydrogen or methyl or, if a, b and c are 1, $R_7$ is hydrogen and Y is —O—, also a group —CH$_2$—CH$_2$—OR$_6$, in which $R_6$ is as defined above, and $Z_2$ is hydrogen, $C_2$-$C_{12}$ aliphatic acyloxy, benzoyloxy which is unsubstituted or monosubstituted or disubstituted by methyl or methoxy, or a $C_2$-$C_{12}$ acylamido group which is unsubstituted or $C_1$-$C_4$ N-alkylsubstituted, or one of the groups —$R_{12}$, —$(CH_2)_d$—$R_{12}$,

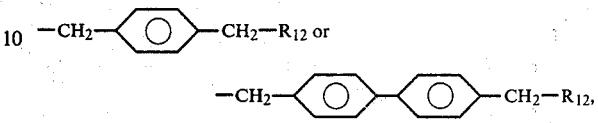

in which d is 2 to 16 and $R_{12}$ is a group of the formula VII, in which $R_1$ and $Z_1$ are as defined above, or $Z_2$ is also a group of the formula VIII, in which X' is —O— or

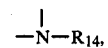

in which $R_{14}$ is hydrogen or $C_1$-$C_4$ alkyl, and $R_{13}$ is —$(CH_2)_e$ or a group

in which e is 0 to 8 and $R_{15}$ and $R_{16}$ independently of one another are hydrogen, $C_1$-$C_4$ alkyl, allyl, benzyl, cyanomethyl, cyanoethyl or a group —$CH_2COOR_{17}$, in which $R_{17}$ is methyl or ethyl, or $Z_2$ is a group of the formulae IX, X or XI, in which $R_6$ and $R_7$ are as defined above, $R_{18}$ is hydrogen, $R_{19}$ is hydrogen, $C_1$-$C_4$ alkyl, allyl or benzyl, $R_{20}$ is $C_1$-$C_4$ alkyl or a group of the formula V, which is as defined above, and $R_{21}$ is $C_2$-$C_6$ alkylene, cyclohexylidene or phenylene, or $Z_2$ is also a group of the formula XIIa

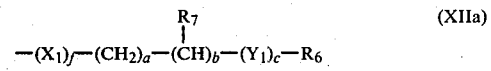

in which a, b, c, $R_6$ and $R_7$ are as defined above and f is 0 or 1 and $X_1$ is —O— or

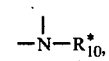

in which $R_{10}^*$ is hydrogen, $C_1$-$C_{12}$ alkyl, cyclohexyl, $C_3$-$C_{14}$ alkoxyalkyl, $C_7$-$C_8$ aralkyl, phenyl which is unsubstituted or monosubstituted or disubstituted by $C_1$-$C_3$ alkyl and/or $C_1$-$C_8$ alkoxy, or, if a, b and c are 1, $R_7$ is hydrogen and Y is —O—, also a group —CH$_2$—CH$_2$—OR$_6$, in which $R_6$ is as defined above, and $R_{10}^*$ is also a group VI, in which $R_1$ is as defined above and $R_{11}$ is hydrogen, methyl or allyl, and $Y_1$ is —O— or

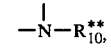

in which $R_{10}*$ is hydrogen, $C_1$-$C_8$ alkyl or phenyl, or $Z_2$ is also one of the groups XIII or XIV, in which $R_6$ is as defined above and $R_{22}$ and $R_{23}$ independently of one another are hydrogen, methyl or ethyl, and $Z_3$ is hydrogen or cyano, or $Z_2$ and $Z_3$ together are one of the formulae XV, XVI or XVII, in which $R_6$ is as defined above and $R_{24}$ is hydrogen, methyl or ethyl and $R_{25}$ is hydrogen, $C_1$-$C_{12}$ alkyl, $C_3$-$C_8$ alkenyl or a group —$CH_2COOR_{26}$ or —$CH_2$—$CH(R_8)$—$OR_6$, in which $R_6$ and $R_8$ are as defined above and $R_{26}$ is $C_1$-$C_{12}$ alkyl, and m is 0, 1 or 2 and A is $H_2O$ or an amine of the formula XVIII, in which $R_{27}$ is unsubstituted or —OH—substituted $C_1$-$C_{18}$ alkyl, $C_5$-$C_{12}$ cycloalkyl, unsubstituted or $C_1$-$C_{12}$ alkylsubstituted $C_6$-$C_{10}$ aryl or $C_7$-$C_{20}$ aralkyl, a substituted or unsubstituted aminoalkyl group having 1-8 C atoms in the alkyl part, or a piperidinyl group, and $R_{28}$ is hydrogen or unsubstituted or —OH—substituted $C_1$-$C_{18}$ alkyl, $C_5$-$C_{12}$ cycloalkyl or a substituted or unsubstituted aminoalkyl group having 1-8 C atoms in the alkyl part, or a piperidinyl group, or $R_{27}$ and $R_{28}$ together with the N atom form a pyrrolidine, piperidine or morpholine ring which is substituted by alkyl groups or is unsubstituted, and $R_{29}$ is hydrogen or unsubstituted or —OH— substituted $C_1$-$C_{18}$ alkyl.

Particularly preferred compounds are those of the formula I in which $M^{q\oplus}$ is $Ca^{2+}$, $Mg^{2+}$, $Zn^{2+}$, $Co^{2+}$, $Ni^{2+}$ or $Al^{3+}$ q is 2 or 3 and r is 1 or 2, the quotient q/r being 1, 1.5, 2 or 3, L is a group of the formula II, in which $R_1$ is hydrogen or methyl and $Z_1$ is hydrogen, $C_1$-$C_4$ alkyl, allyl, $C_2$-$C_6$ alkoxyalkyl, benzyl, acetyl or one of the groups —$CH_2COOR_2$ or —$CH_2$—$CH(R_3)$—$OR_4$ or a group of the formula III, in which $R_2$ is $C_1$-$C_4$ alkyl and $R_3$ is hydrogen and $R_4$ is an aliphatic acyl group having 1-8 C atoms and $R_6$ is a group of the formula V, in which $R_9$ is hydrogen, and $R_7$ is hydrogen and $R_8$ is hydrogen or methyl and a is 0, 1 or 2 and b is 0 or 1 and c is 0 or, if a and/or b differ from 0, is also 1, and X is —O— and Y is —O— or

in which $R_{10}$ is hydrogen or methyl or, if a, b and c are 1 and Y is —O—, also a group —$CH_2$—$CH_2$—$OR_6$, in which $R_6$ is as defined above, and $Z_2$ is hydrogen, $C_2$-$C_7$ aliphatic acyloxy, benzoyloxy which is unsubstituted or monosubstituted by methyl or methoxy, or a $C_2$-$C_7$ acylamido group which is unsubstituted or N-substituted by methyl, or one of the groups

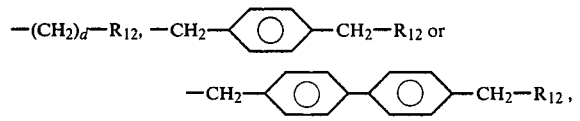

in which d is 2 to 6 and $R_{12}$ is a group of the formula VII, in which $R_1$ and $Z_1$ are as defined above, or $Z_2$ is also a group of the formula VIII, in which X' is —O— or

in which $R_{14}$ is hydrogen or methyl, and $R_{13}$ is —$(CH_2)_e$— or a group

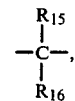

in which e is 0 to 8 and $R_{15}$ and $R_{16}$ independently of one another are hydrogen, $C_1$-$C_4$ alkyl, allyl, benzyl or cyanomethyl, or $Z_2$ is also a group of the formula XI, in which $R_{20}$ is a group of the formula V, which is as defined above, and $R_{21}$ is $C_2$-$C_6$ alkylene or phenylene, or $Z_2$ is also a group of the formula XXIa, in which a, b, c, $R_6$ and $R_7$ are as defined above and f is 0 or 1 and $X_1$ is —O— or

in which $R_{10}*$ is hydrogen, $C_1$-$C_8$ alkyl, cyclohexyl, $C_3$-$C_8$ alkoxyalkyl, $C_7$-$C_8$ aralkyl, phenyl which is unsubstituted or monosubstituted by $C_1$-$C_3$ alkyl and/or $C_1$-$C_2$ alkoxy, or, if a, b and c are 1 and $Y_1$ is —O— also a group —$CH_2$—$CH_2$—$OR_6$, in which $R_6$ is as defined above, and $R_{10}*$ is also a group VI, in which $R_1$ is as defined above and $R_{11}$ is hydrogen or methyl, and $Y_1$ is —O— or

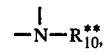

in which $R_{10}*$ is hydrogen, $C_1$-$C_4$ alkyl or phenyl, or $Z_2$ is also one of the groups XIII or XIV, in which $R_6$ is as defined above and $R_{22}$ and $R_{23}$ independently of one another are hydrogen, methyl or ethyl, and $Z_3$ is hydrogen, or $Z_2$ and $Z_3$ together are one of the formulae XV, XVI or XVII, in which $R_6$ is as defined above and $R_{24}$ is hydrogen or methyl and $R_{25}$ is $C_1$-$C_8$ alkyl, allyl or one of the groups —$CH_2$—$COOR_{26}$ or —$CH_2$—$CH(R_8)$—$OR_6$, in which $R_6$ and $R_8$ are as defined above, and $R_{26}$ is $C_1$-$C_8$ alkyl, and m is 0, 1 or 2, and A is $H_2O$ or an amine of the formula XVIII, in which $R_{27}$ and $R_{28}$ independently of one another are $C_1$-$C_8$ alkyl, $C_1$-$C_6$ hydroxyalkyl or a substituted aminoalkyl group of the formula VIIb

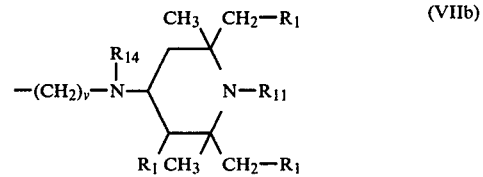

(VIIb)

in which $R_1$, $R_{11}$ and $R_{14}$ are as defined above and v is 1 to 8, or $R_{27}$ and $R_{28}$ together with the N atom form a piperidine group, and $R_{29}$ is hydrogen, $C_1$-$C_8$ alkyl or $C_1$-$C_6$ hydroxyalkyl.

Compounds of particular interest are those of the formula I, in which $M^{q\oplus}$ is $Ca^{2+}$, $Mg^{2+}$, $Zn^{2+}$, $Co^{2+}$, $Ni^{2+}$ or $Al^{3+}$ and q is 2 or 3 and r is 1 or 2, the quotient q/r being 1, 1.5, 2 or 3, and L is a group of the formula II, in which $R_1$ is hydrogen and $Z_1$ is hydrogen, methyl, acetyl or a group of the formula III, in which $R_6$ is a group of the formula V, in which $R_9$ is hydrogen, and $R_7$ is hydrogen and $R_8$ is hydrogen or methyl, and a is 0, 1 or 2 and b is 0 or 1 and c is 0 or, if a and/or b differ from 0, is also 1, X is —O— and Y is

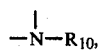

in which $R_{10}$ is hydrogen, and $Z_2$ is hydrogen, $C_2$–$C_7$ aliphatic acyloxy, benzoyloxy, an acylamido group which is unsubstituted or N-substituted by methyl, or one of the groups —$(CH_2)_d$—$R_{12}$,

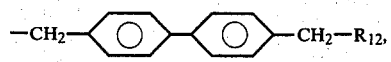

in which d is 2 to 6 and $R_{12}$ is a group of the formula VII, in which $R_1$ and $Z_1$ are as defined above, or $Z_2$ is also a group of the formula VIII, in which X' is —O— or

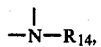

in which $R_{14}$ is hydrogen or methyl, and $R_{13}$ is —$(CH_2)_e$— or a group

in which e is 0 to 8 and $R_{15}$ and $R_{16}$ independently of one another are hydrogen, $C_1$–$C_4$ alkyl, allyl or benzyl, or $Z_2$ is also a group of the formula XI, in which $R_{20}$ is a group of the formula V, which is as defined above, and $R_{21}$ is $C_2$–$C_6$ alkylene, or $Z_2$ is also a group of the formula XIIa, in which a, b, c, $R_6$ and $R_8$ are as defined above and f is 0 or 1 and $X_1$ is —O— or

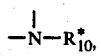

in which $R_{10}^*$ is hydrogen, $C_1$–$C_8$ alkyl, $C_3$–$C_6$ alkoxyalkyl, $C_7$–$C_8$ aralkyl, phenyl which is unsubstituted or monosubstituted by methyl, methoxy or ethoxy, or a group VI, in which $R_1$ is as defined above and $R_{11}$ is hydrogen or methyl, and $Y_1$ is —O—, or $Z_2$ is also one of the groups XIII or XIV, in which $R_6$ is as defined above and $R_{22}$ and $R_{23}$ independently of one another are hydrogen or methyl, and $Z_3$ is hydrogen, or $Z_2$ and $Z_3$ together are one of the formulae XV, XVI or XVII, in which $R_6$ is as defined above and $R_{24}$ is hydrogen and $R_{25}$ is $C_1$–$C_8$ alkyl or one of the groups —$CH_2COOR_{26}$ or —$CH_2$—$CH(R_8)$—$OR_6$, in which $R_6$ and $R_8$ are as defined above, and $R_{26}$ is $C_1$–$C_4$ alkyl, and m is 0, 1 or 2, and A is $H_2O$ or an amine of the formula XVIII, in which $R_{27}$ and $R_{28}$ independently of one another are $C_1$–$C_8$ alkyl, $C_1$–$C_6$ hydroxyalkyl or a group VIIb, in which $R_1$, $R_{11}$ and $R_{14}$ are as defined and v is 1 to 8, or $R_{27}$ and $R_{28}$ together with the N atom form a piperidine group, and $R_{29}$ is hydrogen, $C_1$–$C_8$ alkyl or $C_1$–$C_6$ hydroxyalkyl.

Examples of compounds of the formula I are metal complexes of a metal $M^{q\oplus}$ with one of the following ligands: 2,3,6-trimethyl-2,6-diethyl-4-(1',3'-dioxobutyloxy)-piperidine, 2,2,6,6-tetramethyl-4-(1',3'-dioxopentyloxy)-piperidine, 1-{2''-[N-n-butyl-N-(1',3'-dioxobutyl)]-amino-2''-methylethyl}2,2,6,6-tetramethyl-4-heptanoyloxy-piperidine, 1-[(2'-phenyl-3',6'-dioxa-5'-methyl-7',9'-dioxo)-decyl]-2,2,6,6-tetramethylpiperidine, N,N-dimethyl-N,N'-bis-[1-(3'-oxa-4',6'-dioxo)-heptyl-2,2,6,6-tetramethyl-piperidin-4-yl]-hexamethylenediamine, bis-[1-(3'-oxa-4',6'-dioxo)-heptyl-2,2,6,6-tetramethyl-piperidin-4-yl]-p-xylidene, bis-[1-(3'-oxa-4',6'-dioxo)-heptyl-2,2,6,6-tetramethyl-piperidin-4-yl]adipate, bis-[1-(3'-oxa-4',6'-dioxo)-heptyl-2,2,6,6-tetramethyl-piperidin-4-yl]-n-butyl malonate, bis-[1-(3'-oxa-4',6'-dioxo)-heptyl-2,2,6,6-tetramethyl-piperidin-4-yl]methyl-carbethoxymethyl malonate, 3-n-octyl-7,7,9,9-tetramethyl-8-[(3'-oxa-4',6'-dioxo)-heptyl]-1,3,8-triazaspiro-[4,5]-decane-2,4-dione, 1,2,2,6,6-pentamethyl-4-[1',4',8'-trioxa-9',11'-dioxo-6'-(1'',3''-dioxobutyloxy)]-piperidine, 2,2,6,6-tetramethyl-4-[4'-(1'',3''-dioxobutyloxy)-3'-t.butyl-phenyl]-piperidine, 2,2,6,6-tetramethyl-4-[3',5'-dimethyl-4'-(1'',3''-dioxo-butyloxy)-cyclohexyl]-piperidine, 3-ethyl-3-(1',3'-dioxo-butyloxymethyl)-8,8,10,10-tetramethyl-1,5-dioxa-9-azaspiro[5,5]-undecane, 3-(2'-methyl-3'-oxa-4',6'-dioxoheptyl)-7,7,9,9-tetramethyl-1,3,8-triazaspiro[4,5]-decane-2,4-dione, bis-(2,2,6,6-tetramethyl-piperidin-4-yl)-[2'-methoxymethyl-3'-oxa-4',6'-dioxoheptyl] malonate, bis-(2,2,6,6-tetramethyl-piperidin-4-yl)-methyl-]N-benzyl-N-(1',3'-dioxo-butyl)-aminopropyl] malonate and 2,2,6,6-tetramethyl-4-cyano-4-(1',3'-dioxo-butyloxy)-piperidine.

The ligands listed here can be converted into metal complexes with a metal $M^{q\oplus}$ by one of the processes described below.

The compounds according to the invention are distinguished by the fact that the ligands L, complexed therein, contain at least one radical $R_6$, which is as defined above. The ligands of the formula II used for the synthesis are novel, with the exception of 2,2,6,6-tetramethyl-4-piperidinyl acetoacetate, which also falls under general formula II, and are therefore also a subject of the present invention. The ligands of the formula II can be prepared in a known manner from the analogous compounds of the formula II', in which the substituent $R_6$ in the radicals $Z_1$ and $Z_2$ had been replaced by hydrogen and all the other symbols are as defined for formula II. In particular, the procedure is that the corresponding hydroxy derivatives or amino derivatives are reacted direct or in a solvent with a diketene corresponding to the formula V or with a diketene homologue, the addition of a catalyst usually being unnecessary (c.f. Houben-Weyl "Methoden der organischen Chemie" ("Methods of organic chemistry"), 4th edition, volume 7/4, page 226 et seq.). The diketene is preferably employed in a stoichiometrically equivalent amount or in an excess of up to 10%. Suitable solvents for these reactions are, especially, benzene, toluene, dioxane, dichloroethane, pyridine or dimethylformamide. On the other hand, however, these compounds can be obtained from the intermediates of the formula II', described by the above definition, and β-ketocarboxylates by trans-esterification, or by aminolysis of carboxylates, in a manner which is known per se.

Those intermediates (of the general formula II') in which geminal hydroxyl groups occur can be obtained from 2,2,6,6-tetraalkylpiperidine derivatives which contain primary or secondary amino groups or primary hydroxyl groups and 2,3-epoxy-1-propanol by the known methods for epoxide conversions.

The starting materials of the formula II' are known or, if they are novel, can be prepared according to methods which are known per se and analogously to known compounds. Thus, for example, 4-aminopiperidine derivatives are important starting materials which can be prepared by the processes described in German Offenlegungsschrift No. 2,040,975 or German Offenlegungsschrift No. 2,349,962. Those piperidine derivatives which are substituted on the 4-amino group by an alkylamino group can be prepared in an analogous manner by using a piperidin-4-one derivative as the starting material and reacting this with a monoalkylated diamine.

The piperidine derivatives which contain an alkoxyamino group, especially the oxypropylamino group) in the 4-position are prepared from the corresponding 4-hydroxypiperidine derivatives, which are added onto acrylonitrile by methods which are known per se; the cyano group is then hydrogenated to the corresponding primary amine. Further important starting materials for the preparation of compounds according to formula I are those compounds which at the same time carry a cyano group and a hydroxyl group in the 4-position of the piperidine ring (cyanohydrins), or at the same time carry a cyano group and an amino group in the 4-position of the piperidine ring. The preparation of these compounds is described in U.S. Pat. No. 3,513,170. Hydrogenation of these nitriles then gives, in a known manner, the corresponding 4-methylamino derivatives. $\alpha$-Aminocarboxylates, the $\alpha$-carbon atom of which is in the 4-position in the piperidine derivatives which can be used, are also starting materials for the preparation of compounds of the formula I which are claimed.

The free acids can be prepared from the corresponding piperidin-4-one derivatives by the method of H. T. Bucherer (J. prakt. Chem. 140, 291 (1934)) via hydantoins as intermediates and with subsequent alkaline saponification. Conversion to the corresponding esters is effected in a manner which is known per se with the aid of an acid catalyst.

As described in British Pat. No. 1,337,600, the piperidin-4-one derivatives substituted on the nitrogen in the 1-position can be obtained by protecting the keto group by converting it into a ketal. After introducing the substituent in the 1-position by the conventional methods, the protective group is detached again in a known manner.

The metal complexes of the compounds of the formula I are prepared in a manner which is known per se, for example by dissolving the $\beta$-keto-esters or $\beta$-keto-amides of the formula II in a non-aqueous solvent, preferably a lower alcohol (especially ethanol) and adding an alkali metal alcoholate in an amount equivalent to the enolisable keto groups. The number of mols of a dissolved metal salt necessary to give a molar ratio between the metal ion of valency q+ and the neutralised enolate groups of the ligand molecule of r/q are then added slowly. Solvents which can be used for the metal salt are, in particular, the solvent used initially, or a solvent miscible therewith. The reaction mixture is then stirred at a temperature between 30° and 100° C. for about 1 hour. Metal salts which can be used are, preferably, those which have anions which give sparingly soluble precipitates with the alkali metal ions in the chosen solvents. Precipitation usually takes place on the addition of the metal salt or on subsequent stirring or heating of the reaction mixture. In these cases, the alkali metal salts can be separated off by filtration. Alternatively, they can frequently be separated off after evaporation of the solvent or by extraction of the metal compound with a non-polar solvent. Metal salts which can be used are, especially, chlorides, such as nickel chloride, cobalt-II chloride or dibutyl-tin dichloride. If the salts used are not anhydrous or if the solvents used contain water, the latter can be incorporated into the complex which forms, either as water itself or, alternatively, in the deprotonated form as the hydroxyl ion. In these cases, the end products frequently also contain the alkali metal which was used in the form of an alcoholate in order to form the enolate groups. If the metal salt used is a salt of a carboxylic acid (for example the nickel salt of 2-ethylcaproic acid), the carboxylate ion can frequently not be separated off as the alkali metal salt, or can be only partially separated off as the alkali metal salt, because it is incorporated into the complex as a further ligand anion, in addition to the enolate ions.

Metal alkoxides (for example aluminium triisopropylate) can also be used in place of inorganic metal salts and metal carboxylates as reactants for the formation of metal complexes of a compound of the formula I. In these cases, neutralisation of the $\beta$-keto ester or $\beta$-keto amide with an alkali metal alcoholate is omitted.

If the metal complexes of the compounds of the formula I contain an amine as a further ligand, this can already be added before the alkali metal alcoholate is added, or the metal complex obtained in the manner described above can be dissolved in a solvent containing the amine and this solvent can then be removed again by evaporation.

If the procedure described is followed for the preparation of metal complexes of the compounds of the formula I, mixtures of different complexes, in particular those in which the ratio of the metal ion to the ligand L is greater than r/q, frequently form. These mixtures can also be used as effective stabilisers, like the single compounds of this formula.

According to the present invention, the compounds of the formula I can be used as stabilisers for plastics in order to protect them against damage by the action of oxygen, heat and light. Examples of such plastics are the polymers listed on pages 12–14 of German Offenlegungsschrift No. 2,456,864.

The stabilising of polyolefines, styrene polymers and polyamides and of polyurethanes is of particular importance, and the compounds of the formula I are outstandingly suitable for this. Examples of such polymers are high density and low density polyethylene, polypropylene, ethylene/propylene copolymers, polystyrene, styrene/butadiene/acrylonitrile tercopolymers, mixtures of polyolefines or of styrene polymers, and polyurethanes based on polyethers or polyesters, in the form of lacquers, filaments, films, elastomers or foams.

The stabilisers are added to the plastics in a concentration of 0.01 to 5% by weight, calculated relative to the material to be stabilised. Preferably, 0.03 to 1.5, and particularly preferentially 0.15 to 0.6, % by weight of the compounds, calculated relative to the material to be stabilised, are incorporated into the latter.

Incorporation can be effected after polymerisation, for example by mixing the compounds and, if desired, further additives into the melt by the methods customary in the art, before or during shaping, or by applying the dissolved or dispersed compounds to the polymer, with subsequent evaporation of the solvent if necessary.

The novel compounds can also be added to the plastics to be stabilised in the form of a master batch which contains these compounds, for example in a concentration of 2.5 to 25% by weight.

In the case of crosslinked polyethylene, the compounds are added prior to crosslinking.

The invention therefore also relates to the plastics stabilised by the addition of 0.01 to 5% by weight of a compound of the formula I, which plastics can, if desired, contain yet further known and customary additives. The plastics stabilised in this way can be employed in very diverse forms, for example as films, fibres, tapes or profiles or as binders for lacquers, adhesives or putties.

Examples which may be mentioned of further additives, together with which the stabilisers which can be used according to the invention can be employed, are: antioxidants, such as simple 2,6-dialkylphenols, derivatives of alkylated hydroquinones, hydroxylated thiodiphenyl ethers, alkylidene-bisphenols, O-, N- and S-benzyl compounds, hydroxybenzylated malonates, hydroxybenzyl-aromatic compounds, s-triazine compounds, amides of $\beta$-(3,5-di-tert.-butyl-4-hydroxyphenyl)-propionic acid, esters of $\beta$-(3,5-di-tert.-butyl-4-hydroxyphenyl)-propionic acid, esters of $\beta$-(5-tert.-butyl-4-hydroxy-3-methylphenyl)-propionic acid, esters of 3,5-di-tert.-butyl-4-hydroxyphenylacetic acid, acylaminophenols, benzylphosphonates, aminoaryl derivatives, UV absorbers and light stabilisers, such as 2-(2'-hydroxyphenyl)-benztriazoles, 2,4-bis-(2'-hydroxyphenyl)-6-alkyl-s-triazines, 2-hydroxybenzophenones and 1,3-bis-(2'-hydroxybenzoyl)-benzenes, esters of substituted or unsubstituted benzoic acids, acrylates and, furthermore, nickel compounds, sterically hindered amines, oxalic acid diamides, metal deactivators, phosphites, compounds which destroy peroxide, polyamide stabilisers, basic Co stabilisers, PVC stabilisers, nucleating agents or other additives, for example plasticisers, lubricants, emulsifiers, fillers, carbon black, asbestos, kaolin, talc, glass fibres, pigments, optical brighteners, flameproofing agents and antistatic agents.

Examples of further additives together with which the stabilisers which can be used according to the invention can be employed are given on pages 18–24 of German Offenlegungsschrift No. 2,427,853.

The preparation and use of the compounds according to the invention is described in more detail in the examples which follow. The temperature data always relate to ° C.

EXAMPLES 1 TO 10

The compounds of Examples 1–10 were prepared according to the following general instructions (see Table 1).

0.1 mol of the compounds indicated in column 2 was dissolved in 100 ml of benzene and the amount of diketene ($\beta$-methylene-$\beta$-propiolactone) indicated in column 3, which was mixed with benzene in a ratio of 1:1, was added dropwise in the course of 30 minutes. The temperature of the reaction mixture was not more than 60°. The mixture was then warmed at 60° for 4 hours and the solvent was then evaporated. The residue was worked up by the method described in column 4. The end product indicated in column 5 had the properties indicated in column 6.

TABLE 1

| 1. Example | 2. Starting material | 3. Number of mols of diketene | 4. Working up | 5. End product | 6. Properties |
|---|---|---|---|---|---|
| 1 | 1-(2'-hydroxyethyl)-2,2,6,6-tetramethyl-piperidine | 0.103 | distillation | 1-[2'-(1'',3''-dioxo-butoxy)-ethyl]-2,2,6,6-tetramethyl-piperidine | boiling point 140–142°/1.5 mm Hg |
| 2 | 1-(2'-hydroxyethyl)-2,2,6,6-tetramethyl-4-hydroxy-piperidine | 0.210 | molecular distillation under a high vacuum | 1-[2'-(1'',3''-dioxo-butoxy)-ethyl]-4-(1'',3''-dioxobutoxy)-2,2,6,6-tetramethyl-piperidine | fraction volatile at 55° and 0.01 mm Hg. Elementary analysis: found C 61.78% H 8.35% N 3.74% calculated C 61.77% H 8.46% N 3.79% |
| 3 | 2,2,6,6-tetramethyl-4-hydroxy-piperidine | 0.103 | distillation | 2,2,6,6-tetramethyl-4-(1',3'-dioxobutoxy)-piperidine | boiling point 126–127°/1.5 mm Hg |
| 4 | 1,2,2,6,6-pentamethyl-4-hydroxy-piperidine | 0.103 | distillation | 1,2,2,6,6-pentamethyl-4-(1',3'-dioxobutoxy)-piperidine | boiling point 114–115°/0.7 mm Hg |
| 5 | 2,2,6,6-tetramethyl-4-(N-n-butylamino)-piperidine | 0.103 | distillation | 2,2,6,6-tetramethyl-4-[N-n-butylamine-N-(1',3'-dioxobutyl)]-piperidine | boiling point 187°/0.8 mm Hg |
| 6 | 1,2,2,6,6-pentamethyl-N-(N-n-heptylamino)-piperidine | 0.103 | distillation | 1,2,2,6,6-pentamethyl-4-[N-n-heptylamino-N-(1',3'-dioxobutyl)]-piperidine | boiling point 180–181°/0.9 mm Hg |
| 7 | 2,2,6,6-tetramethyl-4-[N-n-heptyl-N-(2'-hydroxyethyl)-amino]-piperidine | 0.103 | molecular distillation under a high vacuum | 2,2,6,6-tetramethyl-4-N-n-heptyl-N-[2'-(1'',3''-dioxobutoxy)-ethyl]-piperidine | fraction volatile at 75° and 0.01 mm Hg. Elementary analysis: found C 69.9% |

TABLE 1-continued

| Example | Starting material | Number of mols of diketene | Working up | End product | Properties |
|---|---|---|---|---|---|
| | | | | | H 11.2% N 7.4% calculated C 69.65% H 11.18% N 7.06% |
| 8 | 2-hydroxymethyl-7,7,9,9-tetramethyl-1,4-dioxy-8-azaspiro[4.5]decane | 0.103 | distillation | 2-(1',3'-dioxobutoxy-methyl)-7,7,9,9-tetramethyl-1,4-dioxa-8-azaspiro[4.5]-decane | boiling point 136°/0.3 mm Hg |
| 9 | N,N'-bis-(2,2,6,6-tetramethyl-4-piperidyl)-ethylenediamine | 0.210 | recrystallisation from ethylene glycol dimethyl ether | N,N'-bis-(1',3'-dioxobutyl-N,N'-bis-(2,2,6,6-tetramethyl-4-piperidyl)-ethylenediamine | melting point 171° |
| 10 | 1-(2',3'-dihydroxy-propyl)-2,2,6,6-tetramethyl-piperidine | 0.210 | recrystallisation from light benzine (boiling point 110-130°) | 1-[2',3'-bis-(1'',3''-dioxobutoxy)-propyl]-2,2,6,6-tetramethyl-piperidine | melting point 78-80° |
| 11 | 1-(2'-hydroxypropyl)-2,2,6,6-tetramethyl-piperidine | 1.05 | distillation | 1-[2'-(1'',3''-dioxobutyloxy)-propyl]-2,2,6,6-tetramethyl-piperidine | boiling point 136-137°/0.8 mmHg |
| 12 | 2,2,6,6-tetramethyl-4-(N-ethylamino)-piperidine | 1.05 | distillation | 2,2,6,6-tetramethyl-4-[N-ethylamino-N-(1',3'-dioxobutyl)]-piperidine | boiling point 117-118°/0.1 mmHg |
| 13 | 1-allyl-2,2,6,6-tetramethyl-4-hydroxy-piperidine | 1.05 | distillation | 1-allyl-2,2,6,6-tetramethyl-4-(1',3'-dioxobutoxy)-piperidine | boiling point 136-137°/0.8 mmHg found C 68.5% H 9.8%a N 5.0% calculated C 68.29% H 9.67% N 4.98% |
| 14 | 1-n-butyl-2,2,6,6-tetramethyl-4-hydroxy-piperidine | 1.05 | distillation | 1-n-butyl-2,2,6,6-tetramethyl-4-(1',3'-dioxobutoxy)-piperidine | boiling point 147-148°/1.0 mmHg found C 68.9% H 10.5% N 4.8% calculated C 68.88% H 10.20% N 4.73% |
| 15 | 1,4-bis[2',2',6',6'-tetramethyl-4'-hydroxy-piperidino)-butene(2) | 2.10 | recrystallisation from ether | 1,4-bis[2',2',6',6'-tetramethyl-4'-(1'',3''(-dioxobutoxy)-piperidino]-butene(2) | melting point 126-128° found C 67.4% H 9.3% N 5.5% calculated C 67.38% H 9.43% N 5.24% |
| 16 | bis-[1-(2'-hydroxy-ethyl)-2,2,6,6-tetramethyl-piperidin-4-yl]-terephthalate | 2.10 | recrystallisation from acetonitrile | bis[1-(3'-oxa-4',6'-dioxo-heptyl)-2,2,6,6-tetramethyl-piperidin-4-yl]-terephthalate | melting point 124-125° |

EXAMPLES 17 TO 26

The compounds of Examples 17–26 (see Table 2) were prepared according to the following general instructions.

0.1 mol of the compounds indicated in column 2 was dissolved in 200 ml of methanol and 100 ml of a 1.0 molar solution of sodium methylate in methanol were added. 0.05 mol of the metal salts indicated in column 3, dissolved in 160 ml of methanol, was added dropwise to the solutions in the course of 30 minutes. The reaction mixture was then refluxed for 30 minutes and the neutral salt which had precipitated out was separated off by filtration. In Example 14 the reaction mixture was not heated after addition of the metal salt and a neutral salt did not separate out. The resulting solutions were evaporated to dryness and the residue was eluted with the extraction agent indicated in column 4. The extract was evaporated and the residue was dried for 10 hours at a temperature of 60° (exception: Example 14: 40°) and under a pressure of 11 mm Hg. The solid end products indicated in column 5 were obtained in this way and the properties of these products are indicated in column 6.

TABLE 2

| Example | Starting materials compounds according to Example | Metal salts | Extraction agent | End products | Properties Colour | |
|---|---|---|---|---|---|---|
| 17 | 1 | NiCl$_2$ | methylene chloride | 1:2 Ni chelate of 1-[2',1'',3''-dioxobutoxy)-ethyl]-2,2,6,6-tetra- | light green | Ni content 9.4% N content 3.75% |

TABLE 2-continued

| Example | Starting materials compounds according to Example | Metal salts | Extraction agent | End products | Properties Colour | |
|---|---|---|---|---|---|---|
| 18 | 3 | NiCl$_2$ | chloroform | methylpiperidine enolate 1:2 Ni chelate of 2,2,6,6-tetramethyl-4-(1',3'-dioxobutoxy)-piperidine enolate | light green | Ni content 10.1% N content 5.1% |
| 19 | 4 | NiCl$_2$ | methylene chloride | 1:2 Ni chelate of 1,2,2,6,6-pentamethyl-4-(1',3'-dioxobutoxy)-piperidine enolate | light green | Ni content 9.9% N content 4.95% |
| 20 | 4 | Mg (CH$_3$COO$^-$)$_2$ 4 H$_2$O | methylene chloride | 1:2 Mg-II chelate of 1,2,2,6,6-pentamethyl-4-(1',3'-dioxobutoxy)-piperidine enolate containing 1¾ mols of H$_2$O per $_{Mg}$+2 | white | melting point 221-225° content of elements in % found C 59.62% H 9.08% Mg 4.03% calculated C 59.57% H 9.19% Mg 4.30% |
| 21 | 5 | ZnCl$_2$ | hexane | 1:2 Zn-II chelate of 2,2,6,6-tetramethyl-4-[N-n-butylamine-N-(1',3'-dioxobutyl]-piperidine enolate | white | Zn content 10.0% N content 8.5% |
| 22 | 6 | NiCl$_2$ | hexane | 1:2 Ni-chelate of 1,2,2,6,6-pentamethyl-4-[N-n-heptyl-amino-N-(1',3'-dioxobutyl)]-piperidine enolate | light green | Ni content 7.5% N content 7.6% |
| 23 | 8 | NiCl$_2$ | ether | 1:2 Ni chelate of 2-(1',3'-dioxobutoxymethyl)-7,7,9,9-tetramethyl-1,4-dioxy-8-azaspiro[4.5]-decane enolate | light green | Ni content 8.1% N content 4.25% |
| 24 | 10 | NiCl$_2$ | ether | 1:2-Ni-chelate of the 1-[2'-(1'',3''-dioxobutyloxy)propyl]-2,2,6,6-tetramethylpiperidine enolate | light green Ni content 9.8% N content 4.4% | |
| 25 | 11 | NiCl$_2$ | hexane | 1:2 Ni-chelate of the 2,2,6,6-tetramethyl-4[N-ethylamino-N-(1',3'-dioxobutyl)]-piperidine enolate | light green Ni content 8.5% N content 9.1% | |
| 26 | 12 | NiCl$_2$ | hexane | 1:2 Ni-chelate of the 1-allyl-2,2,6,6-tetramethyl-4-(1',3'-dioxobutoxy)-piperidine enolate | light green Ni content 8.7% N content 4.5% | |

EXAMPLE 27

18.5 g (0.05 mol) of 1-[2'-(1'',3''-dioxobutoxy)-ethyl]-4-(1'',3''-dioxobutoxy)-2,2,6,6-tetramethylpiperidine were dissolved in 200 ml of methanol and 5.40 g (0.1 mol) of sodium methylate were added.

16.3 g (0.05 mol) of nickel-II oenenthate (which contained ½ mol of water per mol), dissolved in 330 ml of benzene, were added dropwise to this solution in the course of 30 minutes. The mixture was stirred at room temperature for 4 hours and clarified by filtration and the filtrate was evaporated to dryness. The residue was washed with water and dried for 18 hours at a temperature of 60° and under a pressure of 11 mm Hg, affording the 1:1 nickel-II complex of 1-[2'-(1'',3''-dioxobutoxy)-ethyl]-4-(1'',3''-dioxobutoxy)-2,2,6,6-tetramethylpiperidine dienolate as a monohydrate in the form of a yellowish-green powder.

Elementary analysis: Found: C 51.40%; H 7.22%; N 2.92%; Ni 13.0%; Calculated for the monohydrate: C 51.37%; H 7.02%; N 3.15%; Ni 13.2%.

EXAMPLE 28

25.3 g (0.05 mol) of N,N'-bis-(1',3'-dioxobutyl)-N,N'-bis-(2,2,6,6-tetramethyl-4-piperidyl)-ethylenediamine were dissolved in 500 ml of toluene and 76.9 ml of a 1.3 molar sodium methylate solution (0.1 mol) were added. 16.3 g (0.05 mol) of nickel-II oenanthate (which contained ½ mol of water per mol), dissolved in 330 ml of toluene, were then added dropwise under reflux and the reaction mixture was refluxed for 15 minutes. The precipitated sodium oenanthalate was filtered off and the filtrate was evaporated to dryness. The residue was extracted with toluene at room temperature and the extract was evaporated in vacuo. The resulting residue was dried for 10 hours at a temperature of 60° and under a pressure of 11 mm Hg, affording the 1:1 nickel complex of N,N'-bis-(1',3'-dioxobutyl)-N,N'-bis-(2,2,6,6-tetramethyl-4-piperidyl)-ethylenediamine dienol in the form of a light green powder which contains 9.4% of nickel and 9.2% of nitrogen and in which oenanthic acid anions have been coordinatively incorporated, in addition to the said ligand.

EXAMPLE 29

12.1 g (0.05 mole) of 2,2,6,6-tetramethyl-4-(1',3'-dioxobutoxy)-piperidine are dissolved in 400 ml of ethanol and 3.40 g (0.166 mole) of aluminium isopropylate are added. The mixture is heated, giving a clear solution which is refluxed for two hours. The solvent and the liberated isopropanol are evaporated off and the product is dried at a temperature of 60° C. and under a pressure of 11 mm Hg, affording the 1:3 aluminium (II) complex of the 2,2,6,6-tetramethyl-4-(1',3'-dioxybutoxy)-piperidine enolate in the form of a white powder.

Elementary analysis: Found: C 62.33%; H 9.03%; N 5.64%; Al 3.73%; Calculated: C 62.63%; H 8.89%; N 5.62%; Al 3.61%.

EXAMPLE 30

Light protective action in polypropylene fibres 1000 parts of unstabilised polypropylene powder (melt index ~18) are mixed in a drum mixer with 1 part of pentaerythritol tetrakis[3-(3,5-di-tert-butyl-4-hydroxyphenyl)propionate] and with 3 parts of the additives listed in the table. The mixture is then extruded in an extruder at 220° C. and granulated. The resulting granulate is spun to a 130/37 denier monofilament in a laboratory melt spinning machine at a maximum temperature of 270° C. and a speed of 300 m/minute. This monofilament is drawn and twisted in a draw twister. The draw ratio is 1:5.6 and the twist count is 15/meter, so that finally multifilaments of 130/37 denier are obtained. These multifilaments are mounted on white cardboard and exposed in a xenotest 1200.

The exposure time until 50% loss of ultimate tensile strength is taken as index of the protective action. The results are reported in Table 3.

TABLE 3

| Additive | Time taken until the ultimate tensile strength has been reduced to half of the initial value through exposure in a xenotest 1200 |
| --- | --- |
| none | 35 hours |
| compound 19 | 2050 hours |

EXAMPLE 31

Light protective action in high pressure polyethylene sheets 100 parts of low density polyethylene granulate (0.917) and 0.05 part of a stabiliser of the following table are homogenised for 10 minutes at 180° C. in a Brabender plastograph. The resulting mass is removed from the kneader as quickly as possible and pressed to a sheet having a thickness of 2 to 3 mm in a toggle press. A portion of this sheet is cut out and pressed between two high-gloss rigid aluminium sheets with a hand-operated hydrolic laboratory press for 6 minutes at 170° C. and under a pressure of 12 tons to a sheet having a thickness of 0.1 mm which is immediately chilled in water. Sections each measuring 60×44 mm are then punched out of this sheet and exposed in a xenotest 1200. These blanks are taken out of the exposure apparatus at regular intervals and tested for their carbonyl content in an IR spectrophotometer. The increase of the carbonyl extinction during the exposure is an index of the photooxidative degradation of the polymer (see L. Blavan et al; J. Polymer Sci., Part C, 22, 1059-1071 (1969); J. F. Heacock, J. Polymer Sci., Part A-1, 22, 2921-34 (1969); D. J. Carlsson and D. M. Wiles, Macromolecules 2, 587-606 (1969) and, as previous experience has shown, is allied to a decrease in the mechanical properties of the polymer.

The time taken until a carbonyl extinction of 0.100 is attained serves as index of the protective action.

The results are reported in Table 4.

TABLE 4

| Additive | Exposure time in a xenotest 1200 until a carbonyl extinction of 0.1 has been detected |
| --- | --- |
| none | 270 hours |
| compound 17 | 800 hours |
| 20 | 1840 hours |
| 22 | 2300 hours |

EXAMPLE 32

Light protection of polyethylene blown films 100 parts of low density polyethylene (melt index 0.1–0.3 g/10 min, 190° C., 2.16 kg) were mixed for 2 minutes in a cooled intensive mixer (marketed by Henschel) with one of the additives listed in Table 5 and 0.03 part of 3-(3',5'-di-tert-butyl-4'-hydroxyphenyl)octadecylpropionate. The mixture was extruded from a single screw extruder having a diameter of 35 mm and a length of 700 mm, in the process of which the temperature was adjusted in the first section to 190° C. and in the following three sections to 200° C., then chilled in water and granulated. This granulate was pressed at 190° C. through a blown film extruder having a diameter of 60 mm and a length of 1200 mm. At the exit of the extruder was a tubular die having a diameter of 120 mm and which was adjusted to a temperature of 200° C. The tubular film blown from the extruder was inflated in the ratio of 1:1.8. The rate of discharge was 5 m/min. The sheets had a thickness of 0.2 mm. These sheets were exposed in a xenotest 1200 exposure apparatus.

The carbonyl extinction of the sheets was measured at regular intervals in an infra-red spectrophotometer. The oxidation caused by the carbonyl extinction corresponds in the range of 0.1 to a mechanical damage of the sheet which indicates the onset of unfitness for use. The exposure time until the sheet has attained the carbonyl extinction of 0.1 referred to above is reported in Table 5 and serves as index of the stabilisation.

TABLE 5

| Additive | Exposure time in a xenotest 1200 until a carbonyl extinction of 0.1 has been attained |
| --- | --- |
| none | 320 hours |
| compound 19 | 3650 hours |

EXAMPLE 33

Stabilisation of polypropylene against light 100 parts of polypropylene powder (Moplen, fibre grade, marketed by Montedison), 0.2 part of β-(3,5-di-tert-butyl-4-hydroxyphenyl)octadecylpropionate and 0.25 part of a stabiliser of the following table are homogenised for 10 minutes at 200° C. in a Brabender plastograph. The resulting mass is removed from the kneader as quickly as possible and pressed to a sheet having a thickness of 2 to 3 mm in a toggle press. A portion of this sheet is cut out and pressed between two high-gloss aluminium sheets with a hand-operated hydraulic laboratory press for 6 minutes at 260° C. and under a pressure of 12 tons to a sheet having a thickness of 0.1 mm which is immediately chilled in water. Sections each measuring 60×44 mm are then punched out of this sheet and exposed in a xenotest 1500. These blanks are taken out of the exposure apparatus at regular intervals and tested for their carbonyl content in an IR spectrophotometer. The increase of the carbonyl extinction at 5.85μ during the exposure is an index of the photooxidative degradation of the polymer (see L. Blaban et al., J. Polymer Sci, Part C; 22, 1059–1071 (1969) and, as previous experience has shown, is allied to a decrease in the mechanical properties of the polymer.

The time taken until a carbonyl extinction of about 0.3 is attained, at which the comparison sheet is brittle, serves as index of the protective action.

The protective action of the stabilisers of the invention is evident from the following table:

| Additive | Exposure time in a xenotest 150 until a carbonyl extinction of 0.3 has been detected |
|---|---|
| none | 1050 |
| compound 1 | 3300 |
| compound 4 | 3900 |

Polypropylene ribbons 1000 parts of polypropylene powder (melt index 1.5 g/10 minutes at 230° C., 2160 g) are mixed in a drum mixer with 1 part of pentaerythritol tetrakis-[3-(3',5'-di-tert-butyl-4-hydroxyphenyl)-propionate] and 2.5 parts the additives listed in the following table and subsequently extruded in an extruder at a temperature of 200°–220° and granulated. The resultant granulate is processed to a sheet in the conventional manner using an extruder with slot die. This sheet is cut into ribbons which are then stretched to 6 times their length at elevated temperature. The titre of the ribbons is 700–900 den., and their ultimate tensile strength is 5.5–6.5 g/den.

These ribbons are then exposed in a xenotest 1200. Samples are subjected at regular intervals to a tensile elongation test, in the course of which a progressive decrease in the ultimate tensile strength results with increasing exposure. The exposure time until the ultimate tensile strength has fallen to half the initial value is prolonged by the action of the light stabilisers.

| Additive | Exposure time in a xenotest 1200 until the ultimate tensile strength has been reduced to half the initial value |
|---|---|
| none | 400 |
| compound 9 | 4000 hours |
| 17 | 2800 hours |
| 18 | >5000 hours |
| 19 | 3250 hours |
| 21 | 825 hours |
| 22 | 3000 hours |
| 28 | 2400 hours |
| 29 | >3500 hours |

What is claimed is:
1. A compound of formula I

$$M^{q\oplus} [L^{r\ominus}]_{q/r} \cdot mA \quad (I)$$

wherein $M^{q\oplus}$ is a metal ion carrying a double or triple positive charge and q is 2 or 3 and r is 1 or 2, the quotient q/r being 1, 1.5, 2 or 3, and L is a piperdine, which is substituted by at least one enolate group in the 1-position or 4-position and wherein the ring nitrogen is sterically hindered by alkyl substituents in the adjacent positions, having the formula II

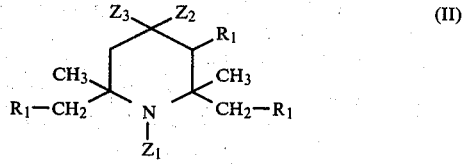

in which $R_1$ is hydrogen or $C_1$–$C_4$ alkyl and $Z_1$ is hydrogen, $C_1$–$C_{12}$ alkyl, $C_3$–$C_8$ alkenyl, $C_3$–$C_4$ alkynyl, $C_2$–$C_{21}$ alkoxyalkyl, $C_7$–$C_8$ aralkyl, an aliphatic acyl group having 1-4 C atoms, or one of the groups —CH$_2$COOR$_2$ or —CH$_2$—CH(R$_3$)—OR$_4$, or a —(CH$_2$)$_4$—R$_5$, —CH$_2$—CH=CH—CH$_2$—R$_5$,

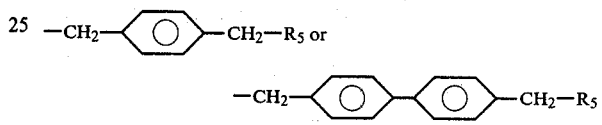

radical or a group of the formula III

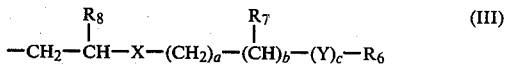

in which $R_2$ is $C_1$–$C_8$ alkyl, $C_3$–$C_6$ alkenyl, phenyl, $C_7$–$C_8$ aralkyl or cyclohexyl and $R_3$ is hydrogen, methyl or phenyl and $R_4$ is an aliphatic $C_1$–$C_{18}$ acyl group, an aromatic $C_7$ acyl group, an araliphatic $C_8$–$C_9$ acyl group or an alicyclic $C_6$–$C_9$ acyl group, in which the aromatic part can be unsubstituted or substituted by chlorine, $C_1$–$C_4$ alkyl, $C_1$–$C_8$ alkoxy and/or hydroxy, and $R_5$ is a group of the formula IV

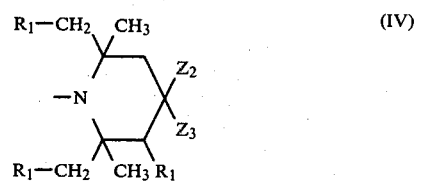

in which $Z_2$ and $Z_3$ are as defined below, and $R_6$ is a group of the formula V

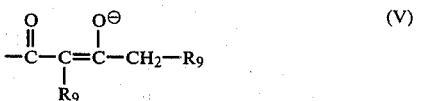

in which $R_9$ is hydrogen or $C_1$–$C_4$ alkyl, and $R_7$ and $R_8$ independently of each other are hydrogen, methyl, phenyl, $C_2$–$C_9$ alkoxymethyl or a —CH$_2$—O—R$_6$ radical, in which $R_6$ is as defined above, and a is 0, 1 or 2 and b is 0 or 1 and c is 0 or, if a and/or b differ from 0, is also 1, and X and Y independently of each other are —O— or in which $R_{10}$ is hydrogen, $C_1$-$C_{12}$ alkyl, $C_3$-$C_8$ alkenyl, cyclohexyl, $C_3$-$C_{21}$ alkoxyalkyl, $C_7$-$C_{13}$ aralkyl, phenyl which is unsubstituted or substituted by $C_1$-$C_8$ alkyl and/or $C_1$-$C_8$ alkoxy, or a group —$CH_2$—$CH_2$—O—$R_6$, in which $R_6$ is as defined above, and $Z_2$ is hydrogen, $C_2$-$C_{18}$ aliphatic acyloxy, benzoyloxy which is unsubstituted or substituted by $C_1$-$C_8$ alkyl or $C_1$-$C_8$ alkoxy, or $C_2$-$C_{18}$ acylamido group which is unsubstituted or $C_1$-$C_8$ N-alkylsubstituted, or one of the groups —$R_{12}$, —$(CH_2)_d$—$R_{12}$, $$-CH_2-\langle \bigcirc \rangle -CH_2-R_{12} \text{ or}$$

$$-CH_2-\langle \bigcirc \rangle -\langle \bigcirc \rangle -CH_2-R_{12},$$

in which d is 2 to 10 and $R_{12}$ is a group of the formula VII (VII)

in which $R_1$ and $Z_1$ are as defined above, or $Z_2$ is also a group of the formula VIII $$-X'-\overset{O}{\underset{}{C}}-R_{13}-\overset{O}{\underset{}{C}}-X'-R_{12} \quad \text{(VIII)}$$

in which $R_{12}$ is as defined above and X' is —O— or $$-\overset{|}{\underset{}{N}}-R_{14},$$

in which $R_{14}$ is hydrogen or $C_1$-$C_4$ alkyl, and $R_{13}$ is —$(CH_2)_e$— or a group $$-\overset{R_{15}}{\underset{R_{16}}{C}}-$$

in which e is 0 to 8 and $R_{15}$ and $R_{16}$ independently of one another are hydrogen, $C_1$-$C_{12}$ alkyl, $C_3$-$C_8$ alkenyl, $C_7$-$C_{11}$ aralkyl, cyanomethyl, cyanoethyl or a group —$CH_2COOR_{17}$, in which $R_{17}$ is methyl or ethyl, or $Z_2$ is one of the groups $$-O-\overset{O}{\underset{}{C}}-\overset{R_{18}}{\underset{CH_2}{C}}-\overset{O}{\underset{}{C}}-O-R_{12} \quad \text{(IX)}$$
$$\underset{R_7-CH-O-R_6}{}$$

$$-O-\overset{O}{\underset{}{C}}-\overset{R_{18}}{\underset{(CH_2)_3}{C}}-\overset{O}{\underset{}{C}}-O-R_{12} \text{ or} \quad \text{(X)}$$
$$\underset{\overset{N}{\underset{R_{19}\quad R_6}{}}}{}$$

$$-\overset{R_{20}}{\underset{R_{21}}{N}}-R_{21}-\overset{R_{20}}{\underset{R_{12}}{N}}- \quad \text{(XI)}$$

in which $R_6$, $R_7$ and $R_{12}$ are as defined above and $R_{18}$ is hydrogen, $C_1$-$C_8$ alkyl, allyl, phenyl or benzyl and $R_{19}$ is hydrogen, $C_1$-$C_8$ alkyl, allyl or benzyl and $R_{20}$ is $C_1$-$C_4$ alkyl or a group of the formula V which is as defined above, and $R_{21}$ is $C_2$-$C_6$ alkylene, cyclohexylidene, phenylene, diphenylene, 4,4'-diphenylene oxide or 4,4'-diphenylenemethane, or $Z_2$ is also a group of the formulae XII, XIII or XIV $$-(X)_f-(CH_2)_{a'}-\overset{R_8}{\underset{}{(CH)}}_{b'}-(Y)_c-(CH_2)_a-\overset{R_7}{\underset{}{(CH)}}_{b}-(O)_g-R_6 \quad \text{(XII)}$$

(XIII)
$$-\langle \bigcirc \rangle -OR_6 \text{ or}$$
with $R_{23}$ and $R_{22}$ substituents (XIV)
$$-\langle \bigcirc_H \rangle -OR_6$$
with $R_{23}$ and $R_{22}$ substituents in which a, b, c, X, Y, $R_6$, $R_7$ and $R_8$ are as defined above and f, a' and b' are 0 or 1 and g is 0 or, if a' and/or b' differ from 0, is also 1, and $R_{22}$ and $R_{23}$ independently of one another are hydrogen, $C_1$-$C_4$ alkyl, cyclohexyl, phenyl, benzyl, α-methylbenzyl or α,α-dimethylbenzyl, and $Z_3$ is hydrogen or cyano, or $Z_2$ and $Z_3$ together are one of the groups XV, XVI or XVII $$\underset{O\diagdown \quad \diagup O}{CH_2-CH-CH_2-O-R_6} \quad \text{(XV)}$$

$$\underset{\overset{CH_2}{\underset{O\diagdown}{}} \quad \overset{CH_2}{\underset{\diagup O}{}}}{R_{24}\diagdown \overset{C}{\underset{}{}} \diagup CH_2-O-R_6 \text{ or}} \quad \text{(XVI)}$$

$$\underset{HN\diagdown \quad \diagup C=O}{O=C-N-R_{25}} \quad \text{(XVII)}$$

in which $R_6$ is as defined above and $R_{24}$ is hydrogen, methyl or ethyl and $R_{25}$ is hydrogen, $C_1$-$C_{18}$ alkyl, $C_3$-$C_8$ alkenyl, cyclohexyl, $C_7$-$C_8$ aralkyl or a group —$CH_2$—$COOR_{26}$ or —$CH_2$—$CH(R_8)$—O—$R_6$, in which $R_{26}$ is $C_1$-$C_{18}$ alkyl and $R_6$ and $R_8$ are as defined above, and m is 0, 1 or 2 and A is $H_2O$ or an amine of the formula (XVIII)

$$R_{29}-N\overset{R_{28}}{\underset{R_{27}}{\diagdown}} \quad \text{(XVIII)}$$

in which $R_{27}$ is substituted or unsubstituted alkyl, cycloalkyl, aryl or aralkyl, a substituted or unsubstituted aminoalkyl or piperidinyl group, and $R_{28}$ is hydrogen or substituted or unsubstituted alkyl or cycloalkyl, a substituted or unsubstituted aminoalkyl group or a piperidinyl group, or $R_{27}$ and $R_{28}$ together with the N atom form a pyrrolidine, piperidine or morpholine ring which is substituted by alkyl groups or is unsubstituted, and $R_{29}$ is hydrogen or substituted or unsubstituted alkyl.

2. A compound according to claim 1 of the formula I, wherein $M^{q\oplus}$ is $Mg^{2+}$, $Ca^{2+}$, $Sr^{2+}$, $Ba^{2+}$, $Zn^{2+}$, $Cd^{2+}$, $Al^{3+}$, $Sn^{2+}$, $Cr^{3+}$, $Co^{2+}$, $Ni^{2+}$, $VO^{2+}$, $MoO^{2+}$, $(R^*)_2Sn^{2+}$ or $(CH_2CH_2COOR^*)_2Sn^{2+}$, in which $R^*$ is $C_1$-$C_8$ alkyl and q is 2 or 3 and r is 1 or 2, the quotient q/r being 1, 1.5, 2 or 3, and L is a group of the formula II, in which $R_1$ is hydrogen or methyl and $Z_1$ is hydrogen, $C_1$-$C_8$ alkyl, $C_3$-$C_4$ alkenyl, $C_3$ alkynyl, $C_2$-$C_{10}$ alkoxyalkyl, $C_7$-$C_8$ aralkyl, acetyl or one of the groups —$CH_2COOR_2$ or —$CH_2$—$CH(R_3)$—$OR_4$, or a —$(CH_2)_4$—$R_5$, —$CH_2$—$CH$=$CH$—$CH_2$—$R_5$,

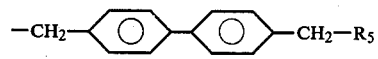

radical or a group of the formula III, in which $R_2$ is $C_1$-$C_4$ alkyl, $C_3$-$C_4$ alkenyl, phenyl, $C_7$-$C_8$ aralkyl or cyclohexyl and $R_3$ is hydrogen or methyl, $R_4$ is an aliphatic acyl group having 1-12 C atoms and $R_5$ is a group of the formula IV, in which $Z_2$ and $Z_3$ are as defined below and $R_1$ is hydrogen, and $R_6$ is a group of the formula V, in which $R_9$ is hydrogen or methyl, and $R_7$ and $R_8$ independently of each other are hydrogen or methyl and a is 0, 1 or 2 and b is 0 or 1 and c is 0 and, if a and/or b differ from 0, is also 1, and X is —O— and Y is —O— or

in which $R_{10}$ is hydrogen or methyl or, if a, b and c are 1, $R_7$ is hydrogen and Y is —O—, also a group —$CH_2$—$CH_2$—$OR_6$, in which $R_6$ is as defined above, and $Z_2$ is hydrogen, $C_2$-$C_{12}$ aliphatic acyloxy, benzoyloxy which is unsubstituted or monosubstituted or disubstituted by methyl or methoxy, or a $C_2$-$C_{12}$ acylamido group which is unsubstituted or $C_1$-$C_4$ N-alkylsubstituted, or one of the groups —$R_{12}$, —$(CH_2)_d$—$R_{12}$,

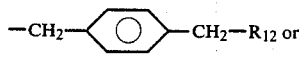

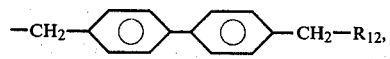

in which d is 2 to 6 and $R_{12}$ is a group of the formula VII, in which $R_1$ and $Z_1$ are as defined above, or $Z_2$ is also a group of the formula VIII, in which X' is —O— or

in which $R_{14}$ is hydrogen or $C_1$-$C_4$ alkyl, and $R_{(13}$ is —$(CH_2)_e$ or a group

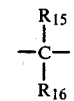

in which e is 0 to 8 and $R_{15}$ and $R_{16}$ independently of one another are hydrogen, $C_1$-$C_4$ alkyl, allyl, benzyl, cyanomethyl, cyanoethyl or a group —$CH_2COOR_{17}$, in which $R_{17}$ is methyl or ethyl, or $Z_2$ is a group of the formulae IX, X or XI, in which $R_6$ and $R_7$ are as defined above and $R_{18}$ is hydrogen, $R_{19}$ is hydrogen, $C_1$-$C_4$ alkyl, allyl or benzyl, $R_{20}$ is $C_1$-$C_4$ alkyl or a group of the formula V, which is as defined above, and $R_{21}$ is $C_2$-$C_6$ alkylene, cyclohexylidene or phenylene, or $Z_2$ is also a group of the formula XIIa

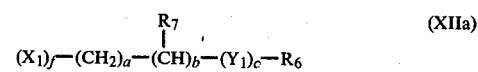

in which a, b, c, $R_6$ and $R_7$ are as defined above and f is 0 or 1 and $X_1$ is —O— or

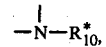

in which $R_{10}^*$ is hydrogen, $C_1$-$C_{12}$ alkyl, cyclohexyl, $C_3$-$C_{14}$ alkoxyalkyl, $C_7$-$C_8$ aralkyl, phenyl which is unsubstituted or monosubstituted or disubstituted by $C_1$-$C_3$ alkyl and/or $C_1$-$C_8$ alkoxy, or, if a, b and c are 1, $R_7$ is hydrogen and Y is —O—, also a group —$CH_2$—$CH_2OR_6$, in which $R_6$ is as defined above and $Y_1$ is —O— or

in which $R_{10}^{**}$ is hydrogen, $C_1$-$C_8$ alkyl or phenyl, or $Z_2$ is also one of the groups XIII or XIV, in which $R_6$ is as defined above and $R_{22}$ and $R_{23}$ independently of each other are hydrogen, methyl or ethyl, and $Z_3$ is hydrogen or cyano, or $Z_2$ and $Z_3$ together are one of the formulae XV, XVI or XVII, in which $R_6$ is as defined above and $R_{24}$ is hydrogen, methyl or ethyl and $R_{25}$ is hydrogen, $C_1$-$C_{12}$ alkyl, $C_3$-$C_8$ alkenyl or a group —$CH_2COOR_{26}$ or —$CH_2$—$CH(R_8)$—$OR_6$, in which $R_6$ and $R_8$ are as defined above and $R_{26}$ is $C_1$-$C_{12}$ alkyl, and m is 0, 1 or 2 and A is $H_2O$ or an amine of the formula XVIII, in which $R_{27}$ is unsubstituted or —OH-substituted $C_1$-$C_{18}$ alkyl, $C_5$-$C_{12}$ cycloalkyl, unsubstituted or $C_1$-$C_{12}$ alkyl-substituted $C_6$-$C_{10}$ aryl or $C_7$-$C_{20}$ aralkyl, a substituted or unsubstituted aminoalkyl group having 1-8 C atoms in the alkyl moiety, or a piperidinyl group, and $R_{28}$ is hydrogen or unsubstituted or —OH-substituted $C_1$-$C_{18}$ alkyl, $C_5$-$C_{12}$ cycloalkyl or a substituted or unsubstituted aminoalkyl group having 1-8 C atoms in the alkyl moiety, or a piperidinyl group, or $R_{27}$ and $R_{28}$ together with the N atom form a pyrrolidine, piperidine or morpholine ring which is substituted by alkyl groups or is unsubstituted, and $R_{29}$ is hydrogen or unsubstituted or —OH-substituted $C_1$-$C_{18}$ alkyl.

3. A compound according to claim 1 of the formula I, wherein $M^{q\oplus}$ is $Ca^{2+}$, $Mg^{2+}$, $Zn^{2+}$, $Co^{2+}$, $Ni^{2+}$ or Al$^{3+}$ and 2 is 2 or 3 and r is 1 or 2, the quotient q/r being 1, 1.5, 2 or 3, and L is a group of the formula II, in which R$_1$ is hydrogen or methyl and Z$_1$ is hydrogen, C$_1$-C$_4$ alkyl, allyl, C$_2$-C$_6$ alkoxyalkyl, benzyl, acetyl or one of the groups —CH$_2$COOR$_2$ or —CH$_2$—CH(R$_3$)—OR$_4$ or a group of the formula III, in which R$_2$ is C$_1$-C$_4$ alkyl and R$_3$ is hydrogen and R$_4$ is an aliphatic acyl group having 1-8 C atoms and R$_6$ is a group of the formula V, in which R$_9$ is hydrogen, and R$_7$ is hydrogen and R$_8$ is hydrogen or methyl and a is 0, 1 or 2 and b is 0 or 1 and c is 0 or, if a and/or b differ from 0, is also 1, and X is —O— and Y is —O— or

in which R$_{10}$ is hydrogen or methyl or, if a, b, and c are 1 and Y is —O—, also a group —CH$_2$—CH$_2$—OR$_6$, in which R$_6$ is as defined above, and Z$_2$ is hydrogen, C$_2$-C$_7$ aliphatic acyloxy, benzoyloxy which is unsubstituted or monosubstituted by methyl or methoxy, or a C$_2$-C$_7$ acylamido group which is unsubstituted or N-substituted by methyl, or one of the groups —(CH$_2$)$_d$—R$_{12}$,

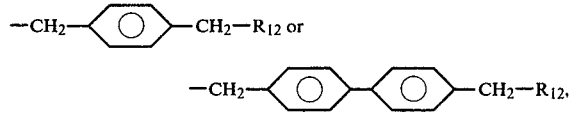

in which d is 2 to 6 and R$_{12}$ is a group of the formula VII, in which R$_1$ and Z$_1$ are as defined above, or Z$_2$ is also a group of the formula VIII, in which X' is —O— or

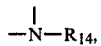

in which R$_{14}$ is hydrogen or methyl, and R$_{13}$ is —(CH$_2$)$_e$— or a group

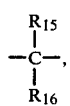

in which e is 0 to 8 and R$_{15}$ and R$_{16}$ independently of each other are hydrogen, C$_1$-C$_4$ alkyl, allyl, benzyl or cyanomethyl, or Z$_2$ is also a group of the formula XI, in which R$_{20}$ is a group of the formula V, which is as defined above, and R$_{21}$ is C$_2$-C$_6$ alkylene or phenylene, or Z$_2$ is also a group of the formula XIIa, in which a, b, c, R$_6$ and R$_8$ are as defined above and f is 0 or 1 and X$_1$ is —O— or

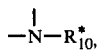

in which R$_{10}$* is hydrogen, C$_1$-C$_8$ alkyl, cyclohexyl, C$_3$-C$_8$ alkoxyalkyl, C$_7$-C$_8$ aralkyl, phenyl which is unsubstituted or monosubstituted by C$_1$-C$_3$ alkyl and/or C$_1$-C$_2$ alkoxy, or, if a, b and c are 1 and Y$_1$ is —O—, also a group —CH$_2$—CH$_2$—OR$_6$, in which R$_6$ is as defined above, R$_{11}$ is hydrogen or methyl, and Y$_1$ is —O— or

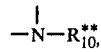

in which R$_{10}$** is hydrogen, C$_1$-C$_4$ alkyl or phenyl, or Z$_2$ is also one of the groups XIII or XIV, in which R$_6$ is as defined above and R$_{22}$ and R$_{23}$ independently of each other are hydrogen, methyl or ethyl, and Z$_3$ is hydrogen, or Z$_2$ and Z$_3$ together are one of the formulae XV, XVI or XVII, in which R$_6$ is as defined above and R$_{24}$ is hydrogen or methyl and R$_{25}$ is C$_1$-C$_8$ alkyl, allyl or one of the groups —CH$_2$—COOR$_{26}$ or —CH$_2$—CH(R$_8$)—OR$_6$, in which R$_6$ and R$_8$ are as defined above, and R$_{26}$ is C$_1$-C$_8$ alkyl, and m is 0, 1 or 2, and A is H$_2$O or an amine of the formula XVIII, in which R$_{27}$ and R$_{28}$ independently of each other are C$_1$-C$_8$ alkyl, C$_1$-C$_6$ hydroxyalkyl or a substituted aminoalkyl group of the formula VIIb

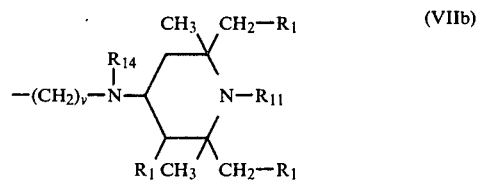

in which R$_1$, R$_{11}$ and R$_{14}$ are as defined above and v is 1 to 8, or R$_{27}$ and R$_{28}$ together with the N atom form a piperidine group, and R$_{29}$ is hydrogen, C$_1$-C$_8$ alkyl or C$_1$-C$_6$ hydroxyalkyl.

4. A compound according to claim 1 of the formula I, wherein M$^{q\oplus}$ is Ca$^{2+}$, Mg$^{2+}$, Zn$^{2+}$, Co$^{2+}$, Ni$^{2+}$ or Al$^{3+}$ and q is 2 or 3 and r is 1 or 2, the quotient q/r being 1, 1.5, 2 or 3, and L is a group of the formula II, in which R$_1$ is hydrogen and Z$_1$ is hydrogen, methyl, acetyl or a group of the formula III, in which R$_6$ is a group of the formula V, in which R$_9$ is hydrogen, and R$_7$ is hydrogen and R$_8$ is hydrogen or methyl, and a is 0, 1 or 2 and b is 0 or 1 and c is 0 or, if a and/or b differ from 0, is also 1, X is —O— and Y is

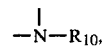

in which R$_{10}$ is hydrogen, and Z$_2$ is hydrogen, C$_2$-C$_7$ aliphatic acyloxy, benzoyloxy, an acylamido group which is unsubstituted or N-substituted by methyl, or one of the groups —(CH$_2$)$_d$—R$_{12}$,

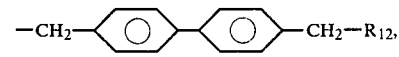

in which d is 2 to 6 and R$_{12}$ is a group of the formula VII, in which R$_1$ and Z$_1$ are as defined above, or Z$_2$ is also a group of the formula VIII, in which X' is —O— or

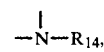

in which R$_{14}$ is hydrogen or methyl, and R$_{13}$ is —(CH$_2$)$_e$— or a group

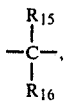

in which e is 0 to 8 and $R_{15}$ and $R_{16}$ independently of each other are hydrogen, $C_1$–$C_4$ alkyl, allyl or benzyl, or $Z_2$ is also a group of the formula XI, in which $R_{20}$ is a group of the formula V, which is as defined above, and $R_{21}$ is $C_2$–$C_6$ alkylene, or $Z_2$ is also a group of the formula XIIa, in which a, b, c, $R_6$ and $R_8$ are as defined above and f is 0 or 1 and $X_1$ is —O— or

in which $R_{10}^*$ is hydrogen, $C_1$–$C_8$ alkyl, $C_3$–$C_6$ alkoxyalkyl, $C_7$–$C_8$ aralkyl, phenyl which is unsubstituted or monosubstituted by methyl, methoxy or ethoxy, $R_{11}$ is hydrogen or methyl, and $Y_1$ is —O—, or $Z_2$ is also one of the groups XIII or XIV, in which $R_6$ is as defined above and $R_{22}$ and $R_{23}$ independently of each other are hydrogen or methyl, and $Z_3$ is hydrogen, or $Z_2$ and $Z_3$ together are one of the formulae XV, XVI or XVII, in which $R_6$ is as defined above and $R_{24}$ is hydrogen and $R_{25}$ is $C_1$–$C_8$ alkyl or one of the groups —$CH_2COOR_{26}$ or —$CH_2$—$CH(R_8)$—$OR_6$, in which $R_6$ and $R_8$ are as defined above, and $R_{26}$ is $C_1$–$C_4$ alkyl, and m is a number 0, 1 or 2, and A is $H_2O$ or an amine of the formula XVIII, in which $R_{27}$ and $R_{28}$ independently of each other are $C_1$–$C_8$ alkyl, $C_1$–$C_6$ hydroxyalkyl or a group VIIb, in which $R_1$, $R_{11}$ and $R_{14}$ are as defined and v is 1 to 8, or $R_{27}$ and $R_{28}$ together with the N atom form a piperidine group, and $R_{29}$ is hydrogen, $C_1$–$C_8$ alkyl or $C_1$–$C_6$ hydroxyalkyl.

5. A compound of the formula I according to claim 1, wherein m is 0.

6. The 2:1 Ni-chelate of the 1-[2',1'',3''-dioxobutoxy)-ethyl]-2,2,6,6-tetramethylpiperidine enol.

7. The 1:2 Ni-chelate of the 1,2,6,6-pentamethyl-4-(1',3'-dioxobutoxy)-piperidine enol.

8. The 1:2 Ni-chelate of the 1,2,6,6-pentamethyl-4-[N-n-heptylamino-N-(1',3'-dioxobutyl)]-piperidine enol.

9. The 1:2 Ni-chelate of the 2,2,6,6-tetramethyl-4-[N-ethylamino-N-(1',3'-dioxobutyl)]-piperidine enol.

10. A polymeric material containing a compound of the formula I according to claim 1.

* * * * *

UNITED STATES PATENT AND TRADEMARK OFFICE
CERTIFICATE OF CORRECTION

PATENT NO. : 4,231,921

DATED : November 4, 1980

INVENTOR(S) : Paul Moser

It is certified that error appears in the above—identified patent and that said Letters Patent is hereby corrected as shown below:

CLAIM 1, COLUMN 28, LINES 21 thru 23 READ:

$$\text{"}-(X)_f-(CH_2)_a-(\overset{R_8}{\underset{|}{C}}H)_b-(Y)_c-(CH_2)_a-(\overset{R_7}{\underset{|}{C}}H)_b-(O)_g-R_6\text{"} \qquad (XII)$$

SHOULD NOW READ:

$$\text{"}-(X)_f-(CH_2)_a-(\overset{R_8}{\underset{|}{C}}H)_b-(Y)_c-(CH_2)_{a'}-(\overset{R_7}{\underset{|}{C}}H)_{b'}-(O)_g-R_6\text{"}.$$

CLAIM 1, COLUMN 28, LINES 24 thru 26 READ:

(XIII)

UNITED STATES PATENT AND TRADEMARK OFFICE
CERTIFICATE OF CORRECTION

PATENT NO. : 4,231,921

DATED : November 4, 1980

INVENTOR(S) : Paul Moser

It is certified that error appears in the above—identified patent and that said Letters Patent is hereby corrected as shown below:

SHOULD NOW READ:

" 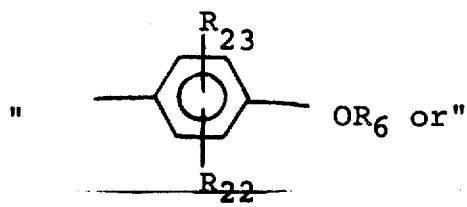 OR$_6$ or"      (XIII)

Signed and Sealed this

Seventh Day of April 1981

[SEAL]

Attest:

RENE D. TEGTMEYER

Attesting Officer     Acting Commissioner of Patents and Trademarks